United States Patent
Derlot et al.

(10) Patent No.: US 10,407,699 B2
(45) Date of Patent: Sep. 10, 2019

(54) **MODIFIED STRAINS OF *TRICHODERMA REESEI* HAVING CELLULASE PROMOTERS WITH XYLASE GENE PROMOTING SEQUENCES**

(71) Applicant: IFP ENERGIES NOUVELLES, Rueil Malmaison (FR)

(72) Inventors: Claire Derlot, Nanterre (FR); Senta Blanquet, Fourqueux (FR)

(73) Assignee: IFP Energies Nouvelles, Rueil Malmaison (FR)

( * ) Notice: Subject to any disclaimer, the term of this patent is extended or adjusted under 35 U.S.C. 154(b) by 0 days.

(21) Appl. No.: 15/568,257

(22) PCT Filed: Apr. 22, 2016

(86) PCT No.: PCT/FR2016/050950
§ 371 (c)(1),
(2) Date: Oct. 20, 2017

(87) PCT Pub. No.: WO2016/170283
PCT Pub. Date: Oct. 27, 2016

(65) Prior Publication Data
US 2018/0112239 A1    Apr. 26, 2018

(30) Foreign Application Priority Data
Apr. 23, 2015 (FR) ...................... 15 53667

(51) Int. Cl.
| | | |
|---|---|---|
| *C12P 7/10* | (2006.01) | |
| *C12N 1/14* | (2006.01) | |
| *C12N 1/38* | (2006.01) | |
| *C12N 15/80* | (2006.01) | |
| *C12N 9/42* | (2006.01) | |

(52) U.S. Cl.
CPC ............... *C12P 7/10* (2013.01); *C12N 1/14* (2013.01); *C12N 1/38* (2013.01); *C12N 9/2437* (2013.01); *C12N 9/2445* (2013.01); *C12N 15/80* (2013.01); *Y02E 50/16* (2013.01)

(58) Field of Classification Search
None
See application file for complete search history.

(56) References Cited

U.S. PATENT DOCUMENTS

| | | |
|---|---|---|
| 2013/0210119 A1 | 8/2013 | Ben Chaabane et al. |
| 2015/0152400 A1 | 6/2015 | Ben Chaabane et al. |

FOREIGN PATENT DOCUMENTS

| | | |
|---|---|---|
| WO | 1999/46362 | 9/1999 |
| WO | 2009/076709 | 6/2009 |
| WO | 2011/109905 | 9/2011 |
| WO | 2012/007650 | 1/2012 |
| WO | 2012/106824 | 8/2012 |
| WO | 2013/190214 | 12/2013 |

OTHER PUBLICATIONS

Accession BBT97467. Apr. 9, 2015 (Year: 2015).*
Accession BBT97467—alignment to SEQ ID No. 3. Apr. 9, 2015 (Year: 2015).*
Accession AY263380. Feb. 21, 2006 (Year: 2006).*
Accession AY263380—alignment to SEQ ID No. 4. Feb. 21, 2006 (Year: 2006).*
The International Search Report for PCT/FR2016/050950 dated Jun. 30, 2016, pp. 1-3.
Rahman, Zinnia et al. "Application of Trichoderma reesei Cellulase and Xylanase Promoters through Homologous Recombination for Enhanced Production of Extracellular [beta]-Glucosidase I" Bioscience Biotechnology Biochemistry (2009) vol. 73(5), pp. 1083-1089.
Herold, Silvia et al. "Xylanase Gene Transcription in Trichoderma reesei is Triggered by Different Inducers Representing Different Hemicellulosic Pentose Polymers" Eukaryotic Cell (2013) vol. 12(3), pp. 390-398.
Ogasawara, W et al. "Cloning, functional expression and promoter analysis of xylanase III gene from Trichoderma reesei" Applied Microbiology and Biotechnology (2006) vol. 72, pp. 995-1003.
Written Opinion of the International Searching Authority for PCT/FR2016/050950 dated Jun. 30, 2016, pp. 1-6.

* cited by examiner

*Primary Examiner* — Christian L Fronda
(74) *Attorney, Agent, or Firm* — McDonnell Boehnen Hulbert & Berghoff LLP

(57) ABSTRACT

The invention relates to strains of *Trichoderma reesei* wherein the inducibility of the promoters of the cellulase genes is modified. The expression of cellulases by these strains of *T. reesei* is induced by the presence of an inducing substrate, said inducing substrate exerting no or little inducing effect on the non-modified strain of *T. reesei*, while keeping inducibility of the cellulases by their inducing substrate.

15 Claims, 5 Drawing Sheets

Figure 1:
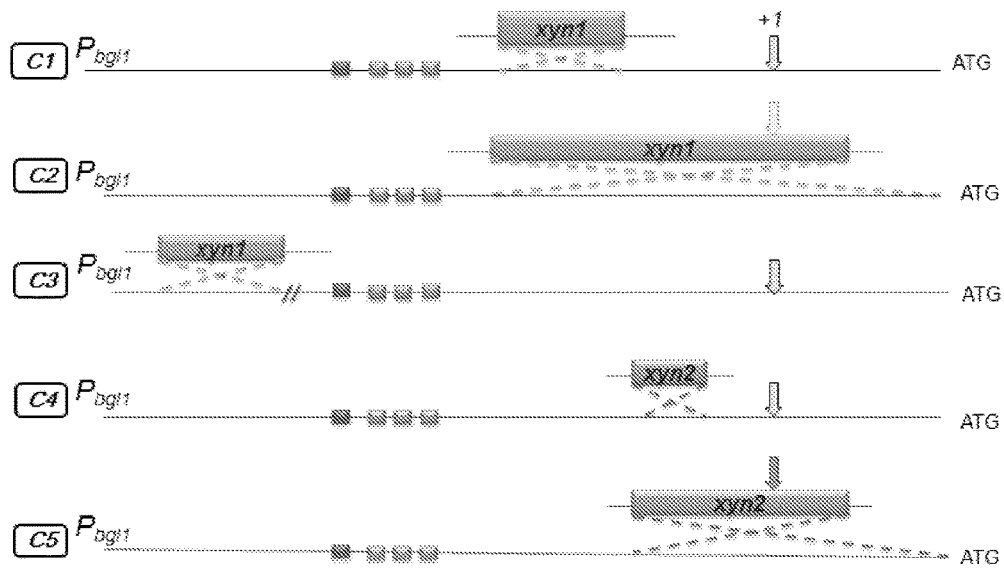

Specification includes a Sequence Listing.

```
                              SEQUENCE LISTING

<160> NUMBER OF SEQ ID NOS: 16

<210> SEQ ID NO 1
<211> LENGTH: 217
<212> TYPE: DNA
<213> ORGANISM: Trichoderma reesei

<400> SEQUENCE: 1
gcagcaaatg gcctcaagca actacgtaaa actccatgag attgcagatg cggcccactg     60
gaatacaaca tcctccgcaa gtccgacatg aagccccttg acttgattgg caggctaaat    120
gcgacatctt agccggatgc accccagatc tggggaacgc gccgcttgag gcccgaagcg    180
ccgggttcga tgcattactg ccatatttca gcagtta                             217

<210> SEQ ID NO 2
<211> LENGTH: 55
<212> TYPE: DNA
<213> ORGANISM: Trichoderma reesei

<400> SEQUENCE: 2
caacttctag actgggtaaa ttggtcaatg gccagccgct cggccgtgcg gagac          55

<210> SEQ ID NO 3
<211> LENGTH: 541
<212> TYPE: DNA
<213> ORGANISM: Trichoderma reesei

<400> SEQUENCE: 3
tctgcagcaa atggcctcaa gcaactacgt aaaactccat gagattgcag atgcggccca     60
ctggaataca acatcctccg caagtccgac atgaagcccc ttgacttgat tggcaggcta    120
aatgcgacat cttagccgga tgcaccccag atctggggaa cgcgccgctt gaggcccgaa    180
gcgccgggtt cgatgcatta ctgccatatt tcagcagtta actaggaccg gcttgtgtcg    240
atattgcggg tggcgttcaa tctattccgg cactcctatg ccgtttgatc cgatacctgg    300
agggcgtgct ttaggcaaaa tgccaagctt cgaggatact gtacgagccg ctttcaacct    360
cacttgatga tgtctgagtt tcatcaagag aattgaagtc aaagctcaaa tcatgatgtg    420
aagaggtttt gaatgtggaa gaattctgca tatataaagc catggaagaa gacgtaaaac    480
tgagacagca agctcaactg catagtatcg acttcaagga aaacacgcac aaataatcat    540
c                                                                    541

<210> SEQ ID NO 4
<211> LENGTH: 235
<212> TYPE: DNA
<213> ORGANISM: Trichoderma reesei

<400> SEQUENCE: 4
caacttctag actgggtaaa ttggtcaatg gccagccgct cggccgtgcg gagacgaggc     60
aagcttgatg aggccaaatt atccgtcaac tgtcttataa aggagcccat gccaaacccc    120
ccctaaagac tcaagaagcc aaacctgaac aaccccagca cctgaacagt catacaaccc    180
ctccaagccc aaaagacaca acaactccta ctagctgaag caagaagaca tcaac         235

<210> SEQ ID NO 5
```

<211> LENGTH: 1250
<212> TYPE: DNA
<213> ORGANISM: Trichoderma reesei

<400> SEQUENCE: 5

```
ccatagtttt ctgtttgcaa accattttg ccattgcgac cgagtttctt tgattaatac      60
tgcttgtgta tggatgatga gtctggaaac actcctcgag gttatgaaag caagacaaag    120
gtctgtgggc acagtttgac gatgccacag ctcgtagggg tctcgggaac gtccaccatc    180
ctccaccatc aacggcgcgt agatgcaagc gataaccata ggtaaaagct tatgtgctcg    240
tgttccacta gcaatgacag tgcagcctga catggctcag atggggcagg tcgattctcg    300
gtaagtttat gctgatcacg gtctttcatg ctaatacgca ctctgccttt tatccatatt    360
cgcacaggcg gctattcgac gcctacaaca gcagaattct cttccattgg tcaattcaca    420
gccagcaaat ttgtgccgca atgccaatcc caatggcttg ttggaagaat ggaggccaag    480
gccctcggct ggcttcttgt cgacatgcgc tcttgaatgt agcttgctgt acattcaag    540
gttggaccac cttcttgttc cgtcgtgcg ccgatgtcca ggacatgaca cttgccgttt    600
gaggcttccc caggttcgct cgcagcaaa tggcctcaag caactacgta aaactccatg    660
agattgcaga tgcggcccac tggaatacaa catcctccgc aagtccgaca tgaagcccct    720
tgacttgatt ggcaggctaa atgcgacatc ttagccggat gcaccccaga tctggggaac    780
gcgccgcttg aggcccgaag cgccgggttc gatgcattac tgccatattt cagcagttag    840
atcatggctg cagtttgtga gcggtcacaa tcgccatctg gtcccagttg gcgaatatg    900
tagccttttca tggggtctag gtgaatggcc cgttatgcta tggccacaga gggagagttc    960
gcgctaccgc ttggtcgagg aaatgatcgc ccacggcctc aaatcgtaaa tctcggtgtg   1020
ggtaggagtg caacgatggg atttggccgc aatgctgccg agcccgagtg tttctgcaac   1080
gttatccagg agatttgcgc ttgcccaaga gggagttgac ggggagagtc ccaactggtt   1140
ccttcagtaa cgccacccctg gcagactata aacttgtgg acaagactct gctttgttga   1200
gttcttccta ccagtcttga ccaagaccat tctgttgagc ccaatcagaa              1250
```

<210> SEQ ID NO 6
<211> LENGTH: 1200
<212> TYPE: DNA
<213> ORGANISM: Trichoderma reesei

<400> SEQUENCE: 6

```
atgacaaacg ggtagagtag ttaatgatgg aataggaaga ggccatagtt ttctgtttgc      60
aaaccatttt tgccattgcg accgagtttc tttgattaat actgcttgtg tatggatgat    120
gagtctggaa acactcctcg aggttatgaa agcaagacaa aggtctgtgg cacagtttg    180
acgatgccac agctcgtagg ggtctcggga acgtccacca tcctccacca tcaacggcgc    240
gtagatgcaa gcgataacca taggtaaaag cttatgtgct cgtgttccac tagcaatgac    300
agtgcagcct gacatggctc agatggggca ggtcgattct cggtaagttt atgctgatca    360
cggtctttca tgctaatacg cactctgcct tttatccata ttcgcacagg cggctattcg    420
acgcctacaa cagcagaatt ctcttccatt ggtcaattca gccagcaa atttgtgccg    480
caatgccaat cccaatggct tgttggaaga atggaggcca aggccctcgg ctggcttctt    540
gtcgacatgc ggtcttgaat gtagcttgct gttacattca aggttggacc accttcttgt    600
tccgtcgtgg cgccgatgtc caggacatga cacttgccgt tgaggcttc ccaggttct    660
ctgcagcaaa tggcctcaag caactacgta aaactccatg agattgcaga tgcggcccac    720
```

```
tggaatacaa catcctccgc aagtccgaca tgaagcccct tgacttgatt ggcaggctaa      780
atgcgacatc ttagccggat gcaccccaga tctggggaac gcgccgcttg aggcccgaag      840
cgccgggttc gatgcattac tgccatattt cagcagttaa ctaggaccgg cttgtgtcga      900
tattgcgggt ggcgttcaat ctattccggc actcctatgc cgtttgatcc gatacctgga      960
gggcgtgctt taggcaaaat gccaagcttc gaggatactg tacgagccgc tttcaacctc     1020
acttgatgat gtctgagttt catcaagaga attgaagtca aagctcaaat catgatgtga     1080
agaggttttg aatgtggaag aattctgcat atataaagcc atggaagaag acgtaaaact     1140
gagacagcaa gctcaactgc atagtatcga cttcaaggaa aacacgcaca aataatcatc     1200
```

<210> SEQ ID NO 7
<211> LENGTH: 1250
<212> TYPE: DNA
<213> ORGANISM: Trichoderma reesei

<400> SEQUENCE: 7

```
ccatagtttt ctgtttgcaa accattttg ccattgcgac cgagtttctt attaatactg       60
cttgtgtatg gatgatgagt ctggaaacac tcctcgaggt tatgaaagca agacaaaggt      120
ctgtgggtct gcagcaaatg gcctcaagca actacgtaaa actccatgag attgcagatg      180
cggcccactg gaatacaaca tcctccgcaa gtccgacatg aagcccttg acttgattgg       240 caggctaaat gcgacatctt agccggatgc accccagatc tggggaacgc gccgcttgag      300
gcccgaagcg ccgggttcga tgcattactg ccatatttca gcagttaact aggaccgatt      360
cgcacaggcg gctattcgac gcctacaaca gcagaattct cttccattgg tcaattcaca      420
gccagcaaat ttgtgccgca atgccaatcc caatggcttg ttggaagaat ggaggccaag      480
gccctcggct ggcttcttgt cgacatgcgg tcttgaatgt agcttgctgt acattcaag       540 gttggaccac cttcttgttc cgtcgtggcg ccgatgtcca ggacatgaca cttgccgttt      600
gaggcttccc caggttcgct tcaaacactt tgcaccagtg atcggaatca tacaaggaat      660
cactgccggg aaaatcgatc agtggcggat ggcatcacga acgctatcgg agaatctcat      720
ggcagagagc atcaggcaac attcggcatc gtttcctacc ctgcggcttc ccaacagccg      780
gtggcagtgc aggagattcc gtaaaagcaa cccgtccatg atggaaggtt ggtgaaccag      840
atcatggctg cagtttgtga gcggtcacaa tcgccatctg gtcccagttg ggcgaatatg      900 tagccttca tggggtctag gtgaatggcc cgttatgcta tggccacaga gggagagttc      960
gcgctaccgc ttggtcgagg aaatgatcgc ccacggcctc aaatcgtaaa tctcggtgtg     1020
ggtaggagtg caacgatggg atttggccgc aatgctgccg agcccgagtg tttctgcaac     1080
gttatccagg agatttgcgc ttgcccaaga gggagttgac ggggagagtc ccaactggtt     1140
ccttcagtaa cgccacccctg gcagactata taacttgtgg acaagactct gctttgttga     1200
gttcttccta ccagtcttga ccaagaccat tctgttgagc ccaatcagaa                 1250
```

<210> SEQ ID NO 8
<211> LENGTH: 1250
<212> TYPE: DNA
<213> ORGANISM: Trichoderma reesei

<400> SEQUENCE: 8

```
ccatagtttt ctgtttgcaa accattttg ccattgcgac cgagtttctt tgattaatac       60
tgcttgtgta tggatgatga gtctggaaac actcctcgag gttatgaaag caagacaaag      120
```

-continued

```
gtctgtgggc acagtttgac gatgccacag ctcgtagggg tctcgggaac gtccaccatc      180
ctccaccatc aacggcgcgt agatgcaagc gataaccata ggtaaaagct tatgtgctcg      240
tgttccacta gcaatgacag tgcagcctga catggctcag atggggcagg tcgattctcg      300
gtaagtttat gctgatcacg gtctttcatg ctaatacgca ctctgccttt tatccatatt      360
cgcacaggcg gctattcgac gcctacaaca gcagaattct cttccattgg tcaattcaca      420
gccagcaaat ttgtgccgca atgccaatcc caatggcttg ttggaagaat ggaggccaag      480
gccctcggct ggcttcttgt cgacatgcgg tcttgaatgt agcttgctgt tacattcaag      540
gttggaccac cttcttgttc cgtcgtggcg ccgatgtcca ggacatgaca cttgccgttt      600
gaggcttccc caggttcgct tcaaacactt tgcaccagtg atcggaatca tacaaggaat      660
cactgccggg aaaatcgatc agtggcggat ggcatcacga acgctatcgg agaatctcat      720
ggcagagagc atcaggcaac attcggcatc gtttcctacc ctgcggcttc ccaacagccg      780
gtggcagtgc aggagattcc gtaaaagcaa cccgtccatg atggaaggtt ggtgaaccag      840
atcatggctg cagtcaactt ctagactggg taaattggtc aatggccagc cgctcggccg      900
tgcggagaca tggggtctag gtgaatggcc cgttatgcta tggccacaga gggagagttc      960
gcgctaccgc ttggtcgagg aaatgatcgc ccacggcctc aaatcgtaaa tctcggtgtg     1020
ggtaggagtg caacgatggg atttggccgc aatgctgccg agcccgagtg tttctgcaac     1080
gttatccagg agatttgcgc ttgcccaaga gggagttgac ggggagagtc ccaactggtt     1140
ccttcagtaa cgccaccctg gcagactata aacttgtggg acaagactct gctttgttga     1200
gttcttccta ccagtcttga ccaagaccat tctgttgagc ccaatcagaa                1250
```

<210> SEQ ID NO 9
<211> LENGTH: 1151
<212> TYPE: DNA
<213> ORGANISM: Trichoderma reesei

<400> SEQUENCE: 9

```
gggttttaat gatgttgtta tgacaaacgg gtagagtagt taatgatgga ataggaagag       60
gccatagttt tctgtttgca aaccattttt gccattgcga ccgagtttct ttgattaata      120
ctgcttgtgt atggatgatg agtctggaaa cactcctcga ggttatgaaa gcaagacaaa      180
ggtctgtggg cacagtttga cgatgccaca gctcgtaggg gtctcgggaa cgtccaccat      240
cctccaccat caacggcgcg tagatgcaag cgataaccat aggtaaaagc ttatgtgctc      300
gtgttccact agcaatgaca gtgcagcctg acatggctca gatggggcag gtcgattctc      360
ggtaagttta tgctgatcac ggtctttcat gctaatacgc actctgcctt ttatccatat      420
tcgcacaggc ggctattcga cgcctacaac agcagaattc tcttccattg gtcaattcac      480
agccagcaaa tttgtgccgc aatgccaatc ccaatggctt gttggaagaa tggaggccaa      540
ggccctcggc tggcttcttg tcgacatgcg gtcttgaatg tagcttgctg ttacattcaa      600
ggttggacca ccttcttgtt ccgtcgtggc gccgatgtcc aggacatgac acttgccgtt      660
tgaggcttcc ccaggttcgc ttcaaacact ttgcaccagt gatcggaatc atacaaggaa      720
tcactgccgg gaaaatcgat cagtggcgga tggcatcacg aacgctatcg gagaatctca      780
tggcagagag catcaggcaa cattcggcat cgtttcctac cctgcggctt cccaacagcc      840
ggtggcagtg caggagattc cgtaaaagca cccgtccat gatggaaggt tggtgaacca      900
gatcatggct gcagtcaact tctagactg gtaaattgg tcaatggcca gccgctcggc      960
cgtgcggaga cgaggcaagc ttgatgaggc caaattatcc gtcaactgtc ttataaagga     1020
```

| | |
|---|---|
| gcccatgcca aaccccccct aaagactcaa gaagccaaac ctgaacaacc ccagcacctg | 1080 |
| aacagtcata caaccccctcc aagcccaaaa gacacaacaa ctcctactag ctgaagcaag | 1140 |
| aagacatcaa c | 1151 |

<210> SEQ ID NO 10
<211> LENGTH: 2666
<212> TYPE: DNA
<213> ORGANISM: Artificial Sequence
<220> FEATURE:
<223> OTHER INFORMATION: Sequence de la cassette utilisee pour la construction C1

<400> SEQUENCE: 10

| | |
|---|---|
| acatctggta caccggcaaa cccgtctacg agtttggcag tggtctcttc tacaccacct | 60 |
| tcaaggagac tctcgccagc cacccccaaga gcctcaagtt caacacctca tcgatcctct | 120 |
| ctgctcctca ccccggatac acttacagcg agcagattcc cgtcttcacc ttcgaggcca | 180 |
| acatcaagaa ctcgggcaag acggagtccc catatacggc catgctgttt gttcgcacaa | 240 |
| gcaacgctgg cccagccccg tacccgaaca agtggctcgt cggattcgac cgacttgccg | 300 |
| acatcaagcc tggtcactct tccaagctca gcatccccat ccctgtcagt gctctcgccc | 360 |
| gtgttgattc tcacggaaac cggattgtat accccggcaa gtatgagcta gccttgaaca | 420 |
| ccgacgagtc tgtgaagctt gagtttgagt tggtgggaga agaggtaacg attgagaact | 480 |
| ggccgttgga ggagcaacag atcaaggatg ctacacctga cgcataaggg ttttaatgat | 540 |
| gttgttatga caaacgggta gagtagttaa tgatggaata ggaagaggcc atagttttct | 600 |
| gtttgcaaac cattttttgcc attgcgaccg agtttctttg attaatactg cttgtgtatg | 660 |
| gatgatgagt ctggaaacac tcctcgaggt tatgaaagca agacaaaggt ctgtgggcac | 720 |
| agtttgacga tgccacagct cgtagggggtc tcgggaacgt ccaccatcct ccaccatcaa | 780 |
| cggcgcgtag atgcaagcga taaccatagg taaaagctta tgtgctcgtg ttccactagc | 840 |
| aatgacagtg cagcctgaca tggctcagat ggggcaggtc gattctcggt aagtttatgc | 900 |
| tgatcacggt ctttcatgct aatacgcact ctgccttta tccatattcg cacaggcggc | 960 |
| tattcgacgc ctacaacagc agaattctct tccattggtc aattcacagc cagcaaattt | 1020 |
| gtgccgcaat gccaatccca atggcttgtt ggaagaatgg aggccaaggc cctcggctgg | 1080 |
| cttcttgtcg acatgcggtc ttgaatgtag cttgctgtta cattcaaggt tggaccacct | 1140 |
| tcttgttccg tcgtggcgcc gatgtccagg acatgacact tgccgtttga ggcttcccca | 1200 |
| ggttcgcttc gcagcaaatg gcctcaagca actacgtaaa actccatgag attgcagatg | 1260 |
| cggcccactg gaatacaaca tcctccgcaa gtccgacatg aagcccttg acttgattgg | 1320 |
| caggctaaat gcgacatctt agccggatgc accccagatc tggggaacgc gccgcttgag | 1380 |
| gcccgaagcg ccgggttcga tgcattactg ccatatttca gcagttagat catggctgca | 1440 |
| gtttgtgagc ggtcacaatc gccatctggt cccagttggg cgaatatgta gcctttcatg | 1500 |
| gggtctaggt gaatggcccg ttatgctatg gccacagagg gagagttcgc gctaccgctt | 1560 |
| ggtcgaggaa atgatcgccc acggcctcaa atcgtaaatc tcggtgtggg taggagtgca | 1620 |
| acgatgggat ttggccgcaa tgctgccgag cccgagtgtt tctgcaacgt tatccaggag | 1680 |
| atttgcgctt gcccaagagg gagttgacgg ggagagtccc aactggttcc ttcagtaacg | 1740 |
| ccaccctggc agactatata acttgtggac aagactctgc tttgttgagt tcttcctacc | 1800 |
| agtcttgacc aagaccattc tgttgagccc aatcagaaat gcgttaccga acagcagctg | 1860 |

| | |
|---|---|
| cgctggcact tgccactggg cccttt gcta gggcagacag tcagtatagc tggtcccata | 1920 |
| ctgggatgtg atatgtatcc tggagacacc atgctgactc ttgaatcaag gtagctcaac | 1980 |
| atcgggggcc tcggctgagg cagttgtacc tcctgcaggg actccatggg aaccgcgta | 2040 |
| cgacaaggcg aaggccgcat tggcaaagct caatctccaa gataaggtcg gcatcgtgag | 2100 |
| cggtgtcggc tggaacggcg gtccttgcgt tggaaacaca tctccggcct caagatcag | 2160 |
| ctatccatcg ctatgccttc aagacggacc cctcggtgtt cgatactcga caggcagcac | 2220 |
| agcctttacg ccgggcgttc aagcggcctc gacgtgggat gtcaatttga tccgcgaacg | 2280 |
| tggacagttc atcggtgagg aggtgaaggc ctcggggatt catgtcatac ttggtcctgt | 2340 |
| ggctgggccg ctgggaaaga ctccgcaggg cggtcgcaac tgggagggct cggtgtcga | 2400 |
| tccatatctc acgggcattg ccatgggtca aaccatcaac ggcatccagt cggtaggcgt | 2460 |
| gcaggcgaca gcgaagcact atatcctcaa cgagcaggag ctcaatcgag aaaccatttc | 2520 |
| gagcaaccca gatgaccgaa ctctccatga gctgtatact tggccatttg ccgacgcggt | 2580 |
| tcaggccaat gtcgcttctg tcatgtgctc gtacaacaag gtcaatacca cctgggcctg | 2640 |
| cgaggatcag tacacgctgc agactg | 2666 |

<210> SEQ ID NO 11
<211> LENGTH: 2956
<212> TYPE: DNA
<213> ORGANISM: Artificial Sequence
<220> FEATURE:
<223> OTHER INFORMATION: Sequence de la cassette utilisee pour la construction C2

<400> SEQUENCE: 11

| | |
|---|---|
| acatctggta caccggcaaa cccgtctacg agtttggcag tggtctcttc tacaccacct | 60 |
| tcaaggagac tctcgccagc cacccccaaga gcctcaagtt caacacctca tcgatcctct | 120 |
| ctgctcctca ccccggatac acttacacg agcagattcc cgtcttcacc ttcgaggcca | 180 |
| acatcaagaa ctcgggcaag acggagtccc catatacggc catgctgttt gttcgcacaa | 240 |
| gcaacgctgg cccagccccg tacccgaaca agtggctcgt cggattcgac cgacttgccg | 300 |
| acatcaagcc tggtcactct tccaagctca gcatccccat ccctgtcagt gctctcgccc | 360 |
| gtgttgattc tcacggaaac cggattgtat accccggcaa gtatgagcta gccttgaaca | 420 |
| ccgacgagtc tgtgaagctt gagtttgagt tggtgggaga agaggtaacg attgagaact | 480 |
| ggccgttgga ggagcaacag atcaaggatg ctacacctga cgcataaggg ttttaatgat | 540 |
| gttgttatga caaacgggta gagtagttaa tgatggaata ggaagaggcc atagttttct | 600 |
| gtttgcaaac catttttgcc attgcgaccg agtttctttg attaatactg cttgtgtatg | 660 |
| gatgatgagt ctggaaacac tcctcgaggt tatgaaagca agacaaaggt ctgtgggcac | 720 |
| agtttgacga tgccacagct cgtaggggtc tcgggaacgt ccaccatcct ccaccatcaa | 780 |
| cggcgcgtag atgcaagcga taaccatagg taaaagctta tgtgctcgtg ttccactagc | 840 |
| aatgacagtg cagcctgaca tggctcagat ggggcaggtc gattctcggt aagtttatgc | 900 |
| tgatcacggt ctttcatgct aatacgcact ctgccttta tccatattcg cacaggcggc | 960 |
| tattcgacgc ctacaacagc agaattctct tccattggtc aattcacagc cagcaaattt | 1020 |
| gtgccgcaat gccaatccca atggcttgtt ggaagaatgg aggccaaggc cctcggctgg | 1080 |
| cttcttgtcg acatgcggtc ttgaatgtag cttgctgtta cattcaaggt tggaccacct | 1140 |
| tcttgttccg tcgtggcgcc gatgtccagg acatgacact tgccgtttga ggcttcccca | 1200 |

```
ggttctctgc agcaaatggc ctcaagcaac tacgtaaaac tccatgagat tgcagatgcg      1260
gcccactgga atacaacatc ctccgcaagt ccgacatgaa gcccttgac ttgattggca      1320 ggctaaatgc gacatcttag ccggatgcac cccagatctg gggaacgcgc cgcttgaggc      1380
ccgaagcgcc gggttcgatg cattactgcc atatttcagc agttaactag gaccggcttg      1440
tgtcgatatt gcgggtggcg ttcaatctat tccggcactc ctatgccgtt tgatccgata      1500
cctggagggc gtgctttagg caaaatgcca agcttcgagg atactgtacg agccgctttc      1560
aacctcactt gatgatgtct gagtttcatc aagagaattg aagtcaaagc tcaaatcatg      1620
atgtgaagag gttttgaatg tggaagaatt ctgcatatat aaagccatgg aagaagacgt      1680
aaaactgaga cagcaagctc aactgcatag tatcgacttc aaggaaaaca cgcacaaata      1740
atcatcatgc gttaccgaac agcagctgcg ctggcacttg ccactgggcc ctttgctagg      1800
gcagacagtc agtatagctg gtcccatact gggatgtgat atgtatcctg agacaccat       1860 gctgactctt gaatcaaggt agctcaacat cgggggcctc ggctgaggca gttgtacctc      1920
ctgcagggac tccatgggga accgcgtacg acaaggcgaa ggccgcattg caaagctca       1980 atctccaaga taaggtcggc atcgtgagcg tgtcggctg gaacggcggt ccttgcgttg       2040
gaaacacatc tccggcctcc aagatcagct atccatcgct atgccttcaa gacggacccc      2100
tcggtgttcg atactcgaca gcagcacag cctttacgcc gggcgttcaa gcggcctcga       2160
cgtgggatgt caatttgatc cgcgaacgtg gacagttcat cggtgaggag gtgaaggcct      2220
cggggattca tgtcatactt ggtcctgtgg ctgggccgct gggaaagact ccgcagggcg      2280
gtcgcaactg ggagggcttc ggtgtcgatc catatctcac gggcattgcc atgggtcaaa      2340
ccatcaacgg catccagtcg gtaggcgtgc aggcgacagc gaagcactat atcctcaacg      2400
agcaggagct caatcgagaa accatttcga gcaacccaga tgaccgaact ctccatgagc      2460
tgtatacttg gccatttgcc gacgcggttc aggccaatgt cgcttctgtc atgtgctcgt      2520
acaacaaggt caataccacc tgggcctgcg aggatcagta cacgctgcag actgtgctga      2580
aagaccagct ggggttccca ggctatgtca tgacggactg gaacgcacag cacacgactg      2640
tccaaagcgc gaattctggg cttgacatgt caatgcctgg cacagacttc aacggtaaca      2700
atcggctctg gggtccagct ctcaccaatg cggtaaatag caatcaggtc cccacgagca      2760
gagtcgacga tatggtgact cgtatcctcg ccgcatggta cttgacaggc caggaccagg      2820
caggctatcc gtcgttcaac atcagcagaa atgttcaagg aaaccacaag accaatgtca      2880
gggcaattgc cagggacggc atcgttctgc tcaagaatga cgccaacatc ctgccgctca      2940
agaagcccgc tagcat                                                      2956
```

<210> SEQ ID NO 12
<211> LENGTH: 2569
<212> TYPE: DNA
<213> ORGANISM: Artificial Sequence
<220> FEATURE:
<223> OTHER INFORMATION: Sequence de la cassette utilisee pour la
      construction C3

<400> SEQUENCE: 12

```
caacagcacc actggctttg ccaaggccat tgctgccgcc aagaagtcgg atgccatcat        60
ctacctcggt ggaattgaca acaccattga acaggagggc gctgaccgca cggacattgc       120
ttggcccggt aatcagctgg atctcatcaa gcagctcagc gaggtcggca aaccccttgt       180
cgtcctgcaa atgggcggtg gtcaggtaga ctcatcctcg ctcaagagca acaagaaggt       240
```

```
caactccctc gtctggggcg gatatcccgg ccagtcggga ggcgttgccc tcttcgacat      300
tctctctggc aagcgtgctc ctgccggccg actggtcacc actcagtacc cggctgagta      360
tgttcaccaa ttcccccaga atgacatgaa cctccgaccc gatggaaagt caaaccctgg      420
acagacttac atctggtaca ccggcaaacc cgtctacgag tttggcagtg gtctcttcta      480
caccaccttc aaggagactc tcgccagcca ccccaagagc ctcaagttca cacctcatc       540 gatcctctct gctcctcacc ccggatacac ttacagcgag cagattcccg tcttcaccttt     600 cgaggccaac atcaagaact cgggcaagac ggagtcccca tatacggcca tgctgtttgt      660
tcgcacaagc aacgctggcc cagccccgta cccgaacaag tggctcgtcg gattcgaccg      720
acttgccgac atcaagcctg gtcactcttc caagctcagc atccccatcc ctgtcagtgc      780
tctcgcccgt gttgattctc acggaaaccg gattgtatac cccggcaagt atgagctagc      840
cttgaacacc gacgagtctg tgaagcttga gtttgagttg gtgggagaag aggtaacgat      900
tgagaactgg ccgttggagg agcaacagat caaggatgct acacctgacg cataagggtt      960
ttaatgatgt tgttatgaca aacgggtaga gtagttaatg atggaatagg aagaggccat      1020
agttttctgt ttgcaaacca ttttttgccat tgcgaccgag tttctttgat taatactgct      1080
tgtgtatgga tgatgagtct ggaaacactc ctcgaggtta tgaaagcaag acaaaggtct      1140
gtgggtctgc agcaaatggc ctcaagcaac tacgtaaaac tccatgagat tgcagatgcg      1200
gcccactgga atacaacatc ctccgcaagt ccgacatgaa gccccttgac ttgattggca      1260
ggctaaatgc gacatcttag ccggatgcac cccagatctg gggaacgcgc cgcttgaggc      1320
ccgaagcgcc gggttcgatg cattactgcc atatttcagc agttaactag gaccgattcg      1380
cacaggcggc tattcgacgc ctacaacagc agaattctct tccattggtc aattcacagc      1440
cagcaaattt gtgccgcaat gccaatccca atggcttgtt ggaagaatgg aggccaaggc      1500
cctcggctgg cttcttgtcg acatgcggtc ttgaatgtag cttgctgtta cattcaaggt      1560
tggaccacct tcttgttccg tcgtggcgcc gatgtccagg acatgacact tgccgtttga      1620
ggcttcccca ggttcgcttc aaacactttg caccagtgat cggaatcata caaggaatca      1680
ctgccgggaa aatcgatcag tggcggatgg catcacgaac gctatcggag aatctcatgg      1740
cagagagcat caggcaacat tcggcatcgt ttcctaccct gcggcttccc aacagccggt      1800
ggcagtgcag gagattccgt aaaagcaacc cgtccatgat ggaaggttgg tgaaccagat      1860
catggctgca gtttgtgagc ggtcacaatc gccatctggt cccagttggg cgaatatgta      1920
gcctttcatg gggtctaggt gaatggcccg ttatgctatg ccacagagg gagagttcgc        1980 gctaccgctt ggtcgaggaa atgatcgccc acggcctcaa atcgtaaatc tcggtgtggg      2040
taggagtgca acgatgggat ttggccgcaa tgctgccgag cccgagtgtt tctgcaacgt      2100
tatccaggag atttgcgctt gcccaagagg gagttgacgg ggagagtccc aactggttcc      2160
ttcagtaacg ccaccctggc agactatata acttgtggac aagactctgc tttgttgagt      2220
tcttcctacc agtcttgacc aagaccattc tgttgagccc aatcagaaat gcgttaccga      2280
acagcagctg cgctgcacct tgccactggg ccctttgcta gggcagacag tcagtatagc      2340
tggtcccata ctgggatgtg atatgtatcc tggagacacc atgctgactc ttgaatcaag      2400
gtagctcaac atcggggggcc tcggctgagg cagttgtacc tcctgcaggg actccatggg      2460
gaaccgcgta cgacaaggcg aaggccgcat tggcaaagct caatctccaa gataaggtcg      2520
gcatcgtgag cggtgtcggc tggaacggcg gtccttgcgt tggaaacac                  2569
```

<210> SEQ ID NO 13
<211> LENGTH: 2481
<212> TYPE: DNA
<213> ORGANISM: Artificial Sequence
<220> FEATURE:
<223> OTHER INFORMATION: Sequence de la cassette utilisee pour la
      construction C4

<400> SEQUENCE: 13

| | | | | | |
|---|---|---|---|---|---|
| gtttgttcgc | acaagcaacg | ctggcccagc | cccgtacccg | aacaagtggc | tcgtcggatt | 60 |
| cgaccgactt | gccgacatca | agcctggtca | ctcttccaag | ctcagcatcc | ccatccctgt | 120 |
| cagtgctctc | gcccgtgttg | attctcacgg | aaaccggatt | gtataccccg | gcaagtatga | 180 |
| gctagccttg | aacaccgacg | agtctgtgaa | gcttgagttt | gagttggtgg | gagaagaggt | 240 |
| aacgattgag | aactggccgt | tggaggagca | acagatcaag | gatgctacac | ctgacgcata | 300 |
| agggttttaa | tgatgttgtt | atgacaaacg | ggtagagtag | ttaatgatgg | aataggaaga | 360 |
| ggccatagtt | ttctgtttgc | aaaccatttt | tgccattgcg | accgagtttc | tttgattaat | 420 |
| actgcttgtg | tatggatgat | gagtctggaa | acactcctcg | aggttatgaa | agcaagacaa | 480 |
| aggtctgtgg | gcacagtttg | acgatgccac | agctcgtagg | ggtctcggga | acgtccacca | 540 |
| tcctccacca | tcaacggcgc | gtagatgcaa | gcgataacca | taggtaaaag | cttatgtgct | 600 |
| cgtgttccac | tagcaatgac | agtgcagcct | gacatggctc | agatgggcca | ggtcgattct | 660 |
| cggtaagttt | atgctgatca | cggtctttca | tgctaatacg | cactctgcct | tttatccata | 720 |
| ttcgcacagg | cggctattcg | acgcctacaa | cagcagaatt | ctcttccatt | ggtcaattca | 780 |
| cagccagcaa | atttgtgccg | caatgccaat | cccaatggct | tgttggaaga | atggaggcca | 840 |
| aggccctcgg | ctggcttctt | gtcgacatgc | ggtcttgaat | gtagcttgct | gttacattca | 900 |
| aggttggacc | accttcttgt | tccgtcgtgg | cgccgatgtc | caggacatga | cacttgccgt | 960 |
| ttgaggcttc | cccaggttcg | cttcaaacac | tttgcaccag | tgatcggaat | catacaagga | 1020 |
| atcactgccg | ggaaaatcga | tcagtggcgg | atggcatcac | gaacgctatc | ggagaatctc | 1080 |
| atggcagaga | gcatcaggca | acattcggca | tcgtttccta | ccctgcggct | tcccaacagc | 1140 |
| cggtggcagt | gcaggagatt | ccgtaaaagc | aacccgtcca | tgatggaagg | ttggtgaacc | 1200 |
| agatcatggc | tgcagtcaac | ttctagactg | ggtaaattgg | tcaatggcca | gccgctcggc | 1260 |
| cgtgcggaga | catgggtct | aggtgaatgg | cccgttatgc | tatggccaca | gagggagagt | 1320 |
| tcgcgctacc | gcttggtcga | ggaaatgatc | gcccacggcc | tcaaatcgta | aatctcggtg | 1380 |
| tgggtaggag | tgcaacgatg | ggatttggcc | gcaatgctgc | cgagcccgag | tgtttctgca | 1440 |
| acgttatcca | ggagatttgc | gcttgcccaa | gagggagttg | acggggagag | tcccaactgg | 1500 |
| ttccttcagt | aacgccaccc | tggcagacta | tataacttgt | ggacaagact | ctgctttgtt | 1560 |
| gagttcttcc | taccagtctt | gaccaagacc | attctgttga | gcccaatcag | aaatgcgtta | 1620 |
| ccgaacagca | gctgcgctgg | cacttgccac | tgggcccttt | gctagggcag | acagtcagta | 1680 |
| tagctggtcc | catactggga | tgtgatatgt | atcctggaga | caccatgctg | actcttgaat | 1740 |
| caaggtagct | caacatcggg | ggcctcggct | gaggcagttg | tacctcctgc | agggactcca | 1800 |
| tggggaaccg | cgtacgacaa | ggcgaaggcc | gcattggcaa | agctcaatct | ccaagataag | 1860 |
| gtcggcatcg | tgagcggtgt | cggctggaac | ggcggtcctt | gcgttggaaa | cacatctccg | 1920 |
| gcctccaaga | tcagctatcc | atcgctatgc | cttcaagacg | gacccctcgg | tgttcgatac | 1980 |
| tcgacaggca | gcacagcctt | tacgccgggc | gttcaagcgg | cctcgacgtg | ggatgtcaat | 2040 |

```
ttgatccgcg aacgtggaca gttcatcggt gaggaggtga aggcctcggg gattcatgtc    2100
atacttggtc ctgtggctgg gccgctggga aagactccgc agggcggtcg caactgggag    2160
ggcttcggtg tcgatccata tctcacgggc attgccatgg gtcaaaccat caacggcatc    2220
cagtcggtag gcgtgcaggc gacagcgaag cactatatcc tcaacgagca ggagctcaat    2280
cgagaaacca tttcgagcaa cccagatgac cgaactctcc atgagctgta tacttggcca    2340
tttgccgacg cggttcaggc caatgtcgct tctgtcatgt gctcgtacaa caaggtcaat    2400
accacctggg cctgcgagga tcagtacacg ctgcagactg tgctgaaaga ccagctgggg    2460
ttcccaggct atgtcatgac g                                              2481

<210> SEQ ID NO 14
<211> LENGTH: 2610
<212> TYPE: DNA
<213> ORGANISM: Artificial Sequence
<220> FEATURE:
<223> OTHER INFORMATION: Sequence de la cassette utilisee pour la
      construction C5

<400> SEQUENCE: 14
aacaagtggc tcgtcggatt cgaccgactt gccgacatca agcctggtca ctcttccaag      60
ctcagcatcc ccatccctgt cagtgctctc gcccgtgttg attctcacgg aaaccggatt     120
gtataccccg gcaagtatga gctagccttg aacaccgacg agtctgtgaa gcttgagttt     180
gagttggtgg gagaagaggt aacgattgag aactggccgt tggaggagca acagatcaag     240
gatgctacac ctgacgcata agggttttaa tgatgttgtt atgacaaacg ggtagagtag     300
ttaatgatgg aataggaaga ggccatagtt ttctgtttgc aaaccatttt tgccattgcg     360
accgagtttc tttgattaat actgcttgtg tatggatgat gagtctggaa acactcctcg     420
aggttatgaa agcaagacaa aggtctgtgg gcacagtttg acgatgccac agctcgtagg     480
ggtctcggga acgtccacca tcctccacca tcaacggcgc gtagatgcaa gcgataacca     540
taggtaaaag cttatgtgct cgtgttccac tagcaatgac agtgcagcct gacatggctc     600
agatggggca ggtcgattct cggtaagttt atgctgatca cggtctttca tgctaatacg     660
cactctgcct tttatccata ttcgcacagg cggctattcg acgcctacaa cagcagaatt     720
ctcttccatt ggtcaattca gccagcaa atttgtgccg caatgccaat cccaatggct      780
tgttggaaga atggaggcca aggccctcgg ctggcttctt gtcgacatgc ggtcttgaat     840
gtagcttgct gttacattca aggttggacc accttcttgt tccgtcgtgg cgccgatgtc     900
caggacatga cacttgccgt ttgaggcttc cccaggttcg cttcaaacac tttgcaccag     960
tgatcggaat catacaagga atcactgccg ggaaaatcga tcagtggcgg atggcatcac    1020
gaacgctatc ggagaatctc atggcagaga gcatcaggca acattcggca tcgtttccta    1080
ccctgcggct tcccaacagc cggtggcagt gcaggagatt ccgtaaaagc aacccgtcca    1140
tgatggaagt tggtgaacc agatcatggc tgcagttcaa cttctagact gggtaaattg     1200
gtcaatggcc agccgctcgg ccgtgcggag acgaggcaag cttgatgagg ccaaattatc    1260
cgtcaactgt cttataaagg agcccatgcc aaaccccccc taaagactca agaagccaaa    1320
cctgaacaac cccagcacct gaacagtcat acaacccctc caagcccaaa agacacaaca    1380
actcctacta gctgaagcaa gaagacatca acatgcgtta ccgaacagca gctgcgctgg    1440
cacttgccac tgggcccttt gctagggcag acagtcagta tagctggtcc catactggga    1500
tgtgatatgt atcctggaga caccatgctg actcttgaat caaggtagct caacatcggg    1560
```

-continued

```
ggcctcggct gaggcagttg tacctcctgc agggactcca tggggaaccg cgtacgacaa    1620
ggcgaaggcc gcattggcaa agctcaatct ccaagataag gtcggcatcg tgagcggtgt    1680
cggctggaac ggcggtcctt gcgttggaaa cacatctccg gcctccaaga tcagctatcc    1740
atcgctatgc cttcaagacg gaccsctcgg tgttcgatac tcgacaggca gcacagcctt    1800
tacgccgggc gttcaagcgg cctcgacgtg ggatgtcaat ttgatccgcg aacgtggaca    1860
gttcatcggt gaggaggtga aggcctcggg gattcatgtc atacttggtc ctgtggctgg    1920
gccgctggga aagactccgc agggcggtcg caactgggag ggcttcggtg tcgatccata    1980
tctcacgggc attgccatgg gtcaaaccat caacggcatc cagtcggtag gcgtgcaggc    2040
gacagcgaag cactatatcc tcaacgagca ggagctcaat cgagaaacca tttcgagcaa    2100
cccagatgac cgaactctcc atgagctgta tacttggcca tttgccgacg cggttcaggc    2160
caatgtcgct tctgtcatgt gctcgtacaa caaggtcaat accacctggg cctgcgagga    2220
tcagtacacg ctgcagactg tgctgaaaga ccagctgggg ttcccaggct atgtcatgac    2280
ggactggaac gcacagcaca cgactgtcca aagcgcgaat tctgggcttg acatgtcaat    2340
gcctggcaca gacttcaacg gtaacaatcg gctctggggt ccagctctca ccaatgcggt    2400
aaatagcaat caggtcccca cgagcagagt cgacgatatg gtgactcgta tcctcgccgc    2460
atggtacttg acaggccagg accaggcagg ctatccgtcg ttcaacatca gcagaaatgt    2520
tcaaggaaac cacaagacca atgtcagggc aattgccagg acggcatcg ttctgctcaa    2580
gaatgacgcc aacatcctgc cgctcaagaa                                      2610
```

<210> SEQ ID NO 15
<211> LENGTH: 1250
<212> TYPE: DNA
<213> ORGANISM: Trichoderma reesei

<400> SEQUENCE: 15

```
ccatagtttt ctgtttgcaa accatttttg ccattgcgac cgagtttctt tgattaatac      60
tgcttgtgta tggatgatga gtctggaaac actcctcgag gttatgaaag caagacaaag     120
gtctgtgggc acagtttgac gatgccacag ctcgtagggg tctcgggaac gtccaccatc     180
ctccaccatc aacggcgcgt agatgcaagc gataaccata ggtaaaagct tatgtgctcg     240
tgttccacta gcaatgacag tgcagcctga catggctcag atggggcagg tcgattctcg     300
gtaagtttat gctgatcacg gtctttcatg ctaatacgca ctctgccttt tatccatatt     360
cgcacaggcg gctattcgac gcctacaaca gcagaattct cttccattgg tcaattcaca     420
gccagcaaat ttgtgccgca atgccaatcc caatggcttg ttggaagaat ggaggccaag     480
gccctcggct ggcttcttgt cgacatgcgg tcttgaatgt agcttgctgt acattcaag      540
gttggaccac cttcttgttc cgtcgtggcg ccgatgtcca ggacatgaca cttgccgttt     600
gaggcttccc caggttcgct tcaaacactt tgcaccagtg atcggaatca tacaaggaat     660
cactgccggg aaaatcgatc agtggcggat ggcatcacga acgctatcgg agaatctcat     720
ggcagagagc atcaggcaac attcggcatc gttttcctacc ctgcggcttc ccaacagccg    780
gtggcagtgc aggagattcc gtaaaagcaa cccgtccatg atggaaggtt ggtgaaccag     840
atcatggctg cagtttgtga gcggtcacaa tcgccatctg gtcccagttg gcgaatatg      900
tagccttca tggggtctag gtgaatggcc cgttatgcta tggccacaga gggagagttc      960
gcgctaccgc ttggtcgagg aaatgatcgc ccacggcctc aaatcgtaaa tctcggtgtg    1020
ggtaggagtg caacgatggg atttggccgc aatgctgccg agcccgagtg tttctgcaac   1080
```

```
gttatccagg agatttgcgc ttgcccaaga gggagttgac ggggagagtc ccaactggtt    1140
ccttcagtaa cgccaccctg gcagactata taacttgtgg acaagactct gctttgttga    1200
gttcttccta ccagtcttga ccaagaccat tctgttgagc ccaatcagaa               1250

<210> SEQ ID NO 16
<211> LENGTH: 230
<212> TYPE: DNA
<213> ORGANISM: Trichoderma reesei

<400> SEQUENCE: 16
tctgcagcaa atggcctcaa gcaactacgt aaaactccat gagattgcag atgcggccca      60
ctggaataca acatcctccg caagtccgac atgaagcccc ttgacttgat tggcaggcta     120
aatgcgacat cttagccgga tgcacccag atctggggaa cgcgccgctt gaggcccgaa     180
gcgccgggtt cgatgcatta ctgccatatt tcagcagtta actaggaccg                230
```

MODIFIED STRAINS OF *TRICHODERMA REESEI* HAVING CELLULASE PROMOTERS WITH XYLASE GENE PROMOTING SEQUENCES

This application is a U.S. national phase of International Application No. PCT/FR2016/050950, filed Apr. 22, 2016, which claims priority from French Patent application no. FR1553667 filed Apr. 23, 2015, the disclosure of each of which is hereby incorporated by reference in its entirety.

FIELD OF THE INVENTION

The invention relates to strains of *Trichoderma reesei* wherein the inducibility of the promoters of the genes involved in the degradation of cellulose is modified.

TECHNOLOGICAL BACKGROUND

The possibility of producing ethanol from cellulose has received a great deal of attention because of the availability of large quantities of raw material as well as the advantage of ethanol as a fuel. The natural cellulosic raw materials for such a process are designated by the term "biomass" or "lignocellulosic biomass". Many types of biomass, for example wood, agricultural residues, herbaceous cultivations and municipal solid waste, have been considered as potential raw materials for the production of biofuel.

Pilot or demonstration or even industrial units for the second-generation production of ethanol by biological method have therefore appeared during the past years. However, production on a very large scale has been restricted by the inefficacy of extraction of fermentable sugars from lignocellulosic biomass.

This is because the plant wall contains very many types of compound that are intimately linked: cellulose and hemicelluloses, sugar polymers, and lignin, a complex compound consisting of phenyl propane units. Lignin is associated with the fibrillar lattice (consisting of cellulose and hemicelluloses) by bonds of the chemical type (in particular ether or ester bonds) and hydrogen bonds, which makes it difficult to access and hydrolyse the fibrillar material.

A physicochemical pretreatment is generally applied to disintegrate this complex structure and to give access to the carbohydrates containing the fermentable sugars, being mainly cellulose. This polymer consists of glucose molecules connected together by β1-4 bonds that are very resistant to degradation or depolymerisation. Once the cellulose has been converted into glucose, the latter can easily be fermented into biofuel, for example ethanol, using a yeast.

Hemicelluloses are heteropolymers mainly consisting of pentose (xylose, arabinose) or hexose (mannose, glucose and galactose) units that may be in their acetylated or methylated forms. There exists a great diversity of hemicelluloses according to the constituents of the main skeleton (generally xylane or mannane) and of the branching components (aromatic residues, glucuronic, galacturonic, acetic etc acids).

The enzymatic degradation of cellulose and hemicelluloses is a slow and ineffective process. Some microorganisms specialise in the hydrolysis of lignocellulose and secrete various glycolytic enzymes. Degradation of cellulose requires three main types of activity:
  exo-β-1,4-glucanases or cellobiohydrolases (CBHs), which cut the polysaccharide chains at their ends and release cellobiose (glucose dimer) units,
  endo-β-1,4-glucanases (EGs), which cut the cellulose chains randomly, thus generating new ends that can be attacked by exoglucanases, and
  β-glucosidases (BGLs), which hydrolyse the cellobiose into two glucose units.

Hemicellulases, which carry out the hydrolysis of hemicelluloses, are of a nature as varied as hemicelluloses. Among these, there are
  xylanases, which cut the xylose chains randomly,
  mannanases, which cleave the mannose chains,
  β-xylosidases and β-mannosidases, which cleave the xylose or mannose dimers respectively, and
  arabinofuranosidases, which cut the xylose-arabinose bonds.

Among the efficient cellulase-secreting microorganisms, there are fungi of the *Trichoderma*, *Aspergillus*, *Humicola* and *Fusarium* genera, as well as bacteria such as *Thermomonospora*, *Bacillus*, *Cellulomonas* and *Streptomyces*.

*Trichoderma reesei* (or *T. reesei*) is a saprophyte filamentous fungus of the ascomycetes division. *T. reesei* is at the present time considered to be the only microorganism capable of meeting world requirements for cellulases for agrofuel applications, because of its high secretion capacities.

At the present time, the best strains can secrete up to 100 g/liter of proteins, mainly represented by cellulases and hemicellulases. The two main cellulases in this degradation cocktail (80% of the proteins secreted) are the cellobiohydrolases CEL7A and CEL6A (formally known as CBH1 and CBH2). This cellulolytic cocktail also contains 5 endoglucanases (CEL7B, CEL5A, CEL5B, CEL12A and CEL45A) and β-glucosidases (mainly BGLI), which are associated with auxiliary proteins supposed to assist degradation of the cellulose, such as swollenin, the proteins CIP1 and CIP2 or the "lytic polysaccharide monooxygenases" (LPMOs or AA9).

In addition to its cellulolytic system, *T. reesei* also has a complex hemicellulolytic system composed of 4 xylanases (XYN1 to 4), a xyloglucanase (CEL74A), a β-xylosidase (BXL1), 3 α-arabinofuranosidases (ABF1 to 3), 2 α-arabinofuranosidases/β-xylosidases, an acetyl xylan esterase (AXE1) and a β-mannanase (MAN1).

However, the cost of producing cellulases remains high and represents one of the economic obstacles to the implementation on an industrial scale of methods for processing biofuels.

Industrially, the optimised production of cellulases by *Trichoderma reesei* is carried out in fed-batch protocol (feeding without drawing off) using a feed solution containing lactose as a sugar inducing the production of cellulases.

Although used industrially, lactose has the drawback of being expensive. To overcome this problem, it has been proposed to reduce the cost of production of cellulases by using sugars coming from hemicelluloses that are released during the physicochemical pretreatment of the biomass (for example steam explosion under acidic conditions) for the propagation of *T. reesei* and the production of enzymes. However, this mixture contains no or few sugars capable of inducing the production of cellulases by *T. reesei*. Consequently it is always necessary to add a certain quantity of lactose.

It had also been proposed to replace lactose with xylose, which is a hydrolysis product of xylanes and one of the main sugars obtained during the biomass pretreatment step, to reduce the production cost. However, the genes of cellulases and the bglI gene in particular, coding for the main extracellular β-glucosidase, are not induced by xylose or other xylane degradation products. Consequently the use of a less expensive inducing sugar such as xylose does not make it possible to reduce the cost of production of cellulases.

Thus, taken overall, the prior art shows an unfulfilled and long awaited need to develop strains of *T. reesei* with improved cellulase-production performance. This is the problem that the present invention sets out to solve.

SUMMARY OF THE INVENTION

The inventors have developed modified strains of *T. reesei*, in which elements regulating the promoting sequences for the genes of the xylases xyn1 and xyn2 were inserted in the cellulase promoters. This modification made it possible to confer the inducibility of xylanases on the cellulase genes.

In other words, the expression of cellulases by these strains of *T. reesei* is induced by the presence of an inducing substrate, said inducing substrate exerting no inducing effect on a wild strain of *T. reesei*, for producing such a cellulase.

Thus, in a first aspect, the invention relates to a strain of *Trichoderma reesei* the genome of which is modified by the insertion of at least one element regulating the promoting sequence for a gene chosen from xyn1 and xyn2, in the promoting sequence for a gene coding for a cellulase, it being understood that:
the element regulating the promoting sequence for the xyn1 gene comprises the sequence represented in SEQ ID NO:1 or the sequence represented in SEQ ID NO:3;
the element regulating the promoting sequence for the xyn2 gene comprises the sequence represented in SEQ ID NO:2 or the sequence represented in SEQ ID NO:4.

Preferentially, said insertion takes place between positions −800 and 0 with respect to the site initiating the translation of the gene coding for said cellulase.

Preferentially, said cellulase is chosen from exo-β-1,4-glucanases or cellobiohydrolases, endo-β-1,4-glucanases and β-glucosidases. More preferentially, said cellulase is β-glucosidase.

In one embodiment, the genome of *T. reesei* is modified so that the promoter of the bglI gene coding for β-glucosidase comprises a sequence chosen from the sequence represented in SEQ ID NO:5, 6, 8 or 9.

Preferentially, the production of cellulases by said strain is inducible by the presence of an inducing substrate chosen from xylane; xylose; oligomers of xylose or xylo-oligomers; arabinose; a composition comprising glucose, xylose, galactose, mannose, cellobiose and acetic acid; and mixtures thereof.

In the context of the invention, the strains of *T. reesei* according to the invention maintain the inducibility of the production of cellulases by the substrates conventionally used, such as lactose or cellulose.

Thus, in a preferred embodiment, the strain of the invention is characterised in that the production of cellulase by said strain is inducible by lactose, cellulose or a mixture of lactose or cellulose with an inducing substrate chosen from: xylane; xylose; oligomers of xylose; arabinose; a composition comprising a mixture of glucose, xylose, galactose, mannose, cellobiose and acetic acid; and mixtures thereof.

In a particular embodiment, the element regulating the promoting sequence for the xyn1 gene comprises the sequence represented in SEQ ID NO:1 and is inserted between positions −628 and −411 with respect to the site initiating the translation of the gene coding for β-glucosidase.

In another embodiment, the element regulating the promoting sequence for the xyn1 comprises the sequence represented in SEQ ID NO:3 and is inserted between positions −633 and 0 with respect to the site initiating the translation of the gene coding for β-glucosidase.

In another embodiment, the element regulating the promoting sequence for the xyn2 gene comprises the sequence represented in SEQ ID NO:2 and is inserted between positions −396 and −341 with respect to the site initiating the translation of the gene coding for β-glucosidase.

In another embodiment, the element regulating the promoting sequence for the xyn2 gene comprises the sequence represented in SEQ ID NO:4 and is inserted between positions −395 and 0 with respect to the site initiating the translation of the gene coding for β-glucosidase.

In a second aspect, the invention relates to a mutation cassette comprising a sequence chosen from the sequence represented in SEQ ID NO:10 to 14, preferentially a sequence chosen from the sequence represented in SEQ ID NO:10, 11, 13 and 14.

In a third aspect, the invention relates to the uses of a strain of *T. reesei* according to the invention, in particular for the production of cellulolytic enzymes, for the hydrolysis of cellulose into glucose, for the production of products biosourced from glucose, or from the production of biofuels.

DETAILED DESCRIPTION OF THE INVENTION

Modified Strains of *T. reesei*

Xylane or the hydrolysis products thereof, xylose or xylobiose, are known to cause the expression of the genes of hemicellulases including xylanases. It has been demonstrated that C5 sugars, such as xylose or arabinose, induce the xylanes xyn1 and xyn2 of *T. reesei* (Mach et al., 1996; Zeilinger et al., 1996).

This induction is achieved through the activation of the transcription factor Xyr1. In the promoter of the xyn1 gene, Xyr1 is fixed to the repeated and inversed unit 5'-GGCTAA-3' spaced by 10 pb. The unit "xyr1" is spoken of Induction requires the simultaneous fixing of a dimer of Xyr1, each monomer being fixed to one of the parts of the repeated-inversed sequence. These elements are situated in a region of 217 pb, lying between −538 and −321 pb upstream of the site of initiation of the translation (ATG) of the xyn1 gene. This region has been designated as containing all the elements providing the regulation of the expression of xyn1 (Rauscher et al., 2006; Zeilinger et al., 1996). This sequence is represented in SEQ ID NO:1.

Concerning the gene xyn2, an element of 55 pb, the "xylanase activating element", which confers the regulation of the gene, has been revealed. This region contains the fixing unit for the Xyr1 factor, as well as the transcription factors ACE2 and HAP2/3/5 (Würleitner et al., 2003). This sequence is represented in SEQ ID NO:2.

It has been demonstrated that a reduction in the quantity of lactose and an increase in the quantity of xylose in the medium leads to an increase in the xylanase activity, but also to a concomitant reduction in the cellulase and β-glucosidase activity (Jourdier et al., 2013).

Thus, at the end of long and tedious work, the inventors succeeded in dispensing with this limitation, conferring the inducibility of the xylanases on the genes of the cellulases by modification of their promoter.

More specifically, the inventors succeeded in inserting elements regulating the promoting sequences for the genes of xylanases xyn1 and xyn2 in the promoters of the genes coding for cellulases. This genetic modification made it possible to develop strains of *T. reesei* wherein the expression of cellulases is induced by the presence of an inducing substrate, said inducing substrate exerting no inducing effect on a wild strain of *T. reesei* for the production of such a cellulase.

This allows the production of a balanced cocktail with stronger cellulase, β-glucosidase and xylanase activities, while using more economical inducing substrates.

Thus the invention relates to a strain of *Trichoderma reesei* the genome of which is modified by the insertion of at least one element regulating the promoting sequence for a gene chosen from xyn1 and xyn2, in the sequence promoting the gene coding for a cellulase, it being understood that:
the element regulating the promoting sequence for the xyn1 gene comprises the sequence represented in SEQ ID NO:1 or the sequence represented in SEQ ID NO:3;
the element regulating the promoting sequence for the xyn2 gene comprises the sequence represented in SEQ ID NO:2 or the sequence represented in SEQ ID NO:4.

*Trichoderma reesei* or *T. reesei* is a cellulolytic filamentous fungus. Because of the ability of *T. reesei* to secrete large quantities of cellulases and hemicellulases, this strain is of great interest in the production of enzymes for the transformation of plant biomass materials into bioproducts useful for industry, such as bioethanol. "Reference strain of *T. reesei*" means a strain of *Trichoderma reesei* chosen from the strains QM6a, NG14, RUTC30 and QM9414. These strains are accessible to the public and in particular have been the subject of filings, respectively under the numbers:
ATCC 13631 (strain QM6a);
ATCC 56767 (strain NG14);
ATCC 56765 (strain RUT C30); and
ATCC 26921 (strain QM9414).

"Strain according to the invention" or "modified strain" is intended to designate indifferently in the present application a strain of *Trichoderma reesei* wherein at least one promoter for a gene coding for a cellulase has been modified.

"Promoter" or "promoting sequence" means a DNA sequence adjacent to the transcription initiation site. The promoter is therefore situated upstream of the initiation site and carries sequence elements recognised by the RNA-polymerase that determines the direction of transcription. This is because the promoter comprises not only sequences defining the transcription initiation site but also consensus sequences of the fixing sites of the polymerase RNA and transcription complexes as well as regulating units recognised by activation or transcription suppression factors.

The inventors muted the promoter for the bglI gene so as to modify the inducibility of the strain. These modifications consist of the insertion of a sequence chosen from the sequences represented in SEQ ID NO:1, 2, 3 and 4. Part of the native sequence of the bglI promoter, for its part, is represented in SEQ ID NO:15. More precisely, SEQ ID NO:15 represents the 1250 pb preceding the initiation site for the translation of the bglI gene in the wild strain of *Trichoderma reesei*.

In a first embodiment, the strain of the invention is characterised in that said insertion takes place between positions −1250 and 0 with respect to the initiation site for the translation of the gene coding for said cellulase.

The reference to the position with respect to the initiation site for translation of a gene means the position of the strain before the insertion of a regulation element, that is to say before mutation. This numbering can therefore easily be established with respect to the native sequence of the promoter of bglI, such as in particular represented in SEQ ID NO:15 for β-glucosidase.

Preferentially, said insertion takes place between positions −1200 and 0, preferably between positions −1100 and 0, preferentially between positions −1000 and 0, preferentially between positions −900 and 0, preferentially between positions −800 and 0, even more preferentially between positions −700 and 0 with respect to the initiation site for the translation of the gene coding for said cellulase.

Preferentially, this insertion takes place between positions −700 and −400 with respect to the initiation site for the translation of the gene coding for said cellulase. Preferentially, this insertion takes place between positions −628 and −411 with respect to the initiation site for the translation of the gene coding for said cellulase. Alternatively, this insertion takes place between positions −400 and −300, more preferentially between positions −396 and −341 with respect to the initiation site for the translation of the gene coding for said cellulase.

In a second embodiment, the strain of the invention is characterised in that said insertion does not take place at positions −1224; −1218; −881; −874; −811; −805 with respect to the initiation site for the translation of the gene of the cellulase.

Without wishing to be bound by the theory, the inventors make the hypothesis according to which the positions:
lying between −1224 and −1218 with respect to the initiation site for the translation of the gene of the cellulase;
lying between −881 and −874 with respect to the initiation site for the translation of the gene of the cellulase;
lying between −811 and −805 with respect to the initiation site for the translation of the gene of the cellulase;
correspond to specific positions for recognition by xyr1. Consequently the insertion of a mutation in the vicinity of these sites may potentially lead to an absence of modification of the induced production of cellulases of the strain.

"Cellulase" means an enzyme suited to the hydrolysis of cellulose and enabling the microorganisms that produce them to use the cellulose as a source of carbon, by hydrolysing this polymer into simple sugars (glucose). Preferentially, said cellulase is chosen from exo-β-1,4-glucanases or cellobiohydrolases, endo-β-1,4-glucanases and β-glucosidases. More preferentially, said cellulase is a β-glucosidase, preferably the one encoded by the bglI gene. Thus said insertion takes place in the promoter of the gene coding for extracellular β-glucosidase, that is to say in the promoter of bglI.

Thus the invention relates to a strain of *Trichoderma reesei* the genome of which is modified by the insertion of at least one element regulating the promoting sequence for a gene chosen from xyn1 and xyn2, in the promoting sequence for the gene coding for β-glucosidase. Preferentially, the HAP2/3/5 and xyr1 units, present on the promoter of the bglI, are not modified and remain intact. The HAP2/3/5 and xyr1 units correspond to nucleic units recognised by the transcription factors XYR1 and HAP2/3/5.

In one embodiment, the genome of the strain of the invention can be modified by substitution of a fragment of the promoter bglI by an element regulating the promoting sequence for a gene xyn1 or xyn2. In other words, the genome of *T. reesei* may be modified by:
firstly, the excision of a fragment of the bglI promoter, and
secondly, the insertion of an element regulating the promoting sequence of a gene xyn1 or xyn2.

The inducibility of the production of cellulases by the strain of *T. reesei* according to the invention is modified. More precisely, this production may be induced by the presence of an inducing substrate, preferentially an inducing sugar, that exerts no or little effect on a wild strain of *T. reesei*.

"Wild strain of *T. reesei*" or "non-modified strain of *T. reesei*" means a strain of *T. reesei* which does not comprise a mutation as described in the present invention, that is to say a strain wherein the promoters of the cellulase genes are not modified. Said wild strain may also be a reference strain of *T. reesei*.

"Induction" means the synthesis of enzymes in response to the appearance of a specific product. It is known that microorganisms prevent the synthesis of enzymes, for example by a metabolic method, in the absence of suitable substrates and that they are ready to synthesise such enzymes if the substrate reappears. The strain according to the invention has the particularity of producing cellulases in the presence of a substrate that is not the substrate of the cellulase thus produced, in particular xylose. This is because xylose does not cause the production of cellulase in wild strains of *T. reesei*. In other words, the inventors have succeeded in developing a strain the inducibility of which is modified with respect to the wild *T. reesei* strain.

"Inducing substrate" means a compound inducing an increase in the expression of the targeted metabolic activity, all experimental conditions being otherwise equal, the metabolic activity is stronger when the inducer is at a suitable concentration than when it is absent or at an unsuitable concentration. In the context of the present invention, said inducing substrate is preferentially a sugar in monomer, oligomer or polymer form.

Preferentially, said inducing substrate is chosen from:
xylane;
xylose;
oligomers of xylose;
arabinose;
a hydrolysate of hemicellulose;
mixtures thereof.

In the context of the invention, the strains of *T. reesei* according to the invention maintain the inducibility of the production of cellulases by the substrates conventionally used, such as lactose or cellulose.

Thus, in the preferred embodiment, the strain of the invention is characterised in that the production of cellulase by said strain is inducible by lactose, cellulose or a mixture of lactose with an inducing substrate chosen from: xylane; xylose; oligomers of xylose; arabinose; a composition comprising glucose, xylose, galactose, mannose, cellobiose and acetic acid; and mixtures thereof.

Preferentially, the strain of the invention is characterised in that the production of cellulase by said strain is inducible by
lactose;
xylose; and a mixture of lactose and xylose.

"Hydrolysate of hemicellulose" means a composition comprising a mixture of glucose, xylose, galactose, mannose, cellobiose and acetic acid.

In a particular embodiment, said inducing substrate is a mixture of xylane, xylose, xylobiose and/or arabinose.

Preferentially, said substrate is the hydrolysate of hemicellulose.

More preferentially, the substrate is xylane.

In one embodiment, the substrate is xylose. Alternatively, said substrate is oligomers of xylose.

"Oligomer of xylose" or "xylo-oligomer" means a solution comprising at least one compound chosen from a dimer, a trimer, a tetramer and a pentamer of xylose.

Preferentially, said oligomer of xylose is xylobiose.

In the context of the invention, the expression "modification of the inducibility of the production of cellulases" refers to the genetic modification of the promoter of a cellulase gene, the consequence of which is that this promoter becomes inducible by an inducing substrate. In other words, the presence of said inducing substrate in the culture medium leads to the production of said cellulase by the modified strain, it being understood that said inducing substrate exerts no or little effect on a wild strain of *T. reesei*.

The particularity of the invention lies in the fact that the genes of the cellulases remain inducible by their own inducing substrates, such as lactose, cellobiose or cellulose.

The inventors have exemplified several different strains of *T. reesei* where the promoter of the bglI gene has been modified. For reasons of clarity, these constructions are referred to as constructions or strains C1, C2, C4 and C5.

In a first embodiment, the genome of *Trichoderma reesei* is modified so that the element regulating the promoting sequence for the xyn1 gene comprising the sequence represented in SEQ ID NO:1 is inserted between the positions −628 and −411 with respect to the initiation site of the translation of the gene coding for β-glucosidase. Preferentially, the element regulating the sequence promoting the xyn1 gene consists of the sequence represented in SEQ ID NO:1. The sequence represented in SEQ ID NO:1 is therefore inserted between positions 622 and 839 of the sequence represented in SEQ ID NO:15.

This modified strain of *T. reesei* is called "construction C1" or "strain C1". In this embodiment, the strain has undergone a replacement of 217 pairs of bases (pb) of the promoter bglI by 217 pb of the element regulating the promoting sequence for the gene xyn1. Consequently the promoter of the gene bglI of the construction C1 comprises the sequence as represented in SEQ ID NO:5. This sequence represents the 1250 pb preceding the initiating site for the translation of the gene bglI in the construction C1.

In a second embodiment, the genome of *Trichoderma reesei* is modified so that the element regulating the promoting sequence for the xyn1 gene comprising the sequence represented in SEQ ID NO:3 is inserted between positions −633 and 0 with respect to the site initiating the translation of the gene coding for β-glucosidase. The reference to the site initiating the translation of the gene coding for β-glucosidase means the position before the insertion of the mutation. Preferentially, the element regulating the promoting sequence for the xyn1 gene consists of the sequence represented in SEQ ID NO:3. The sequence represented in SEQ ID NO:3 is therefore inserted between positions 617 and 1250 of the sequence represented in SEQ ID NO:15.

This modified strain of *T. reesei* is called "construction C2" or "strain C2". In this embodiment, the strain has undergone a replacement of 633 pb of the promotor bglI by 541 pb of the element regulating the promoting sequence for the gene xyn1. In this embodiment, the sequence is juxtaposed with the site initiating the translation of bglI. Consequently the promoter of the gene bglI of the construction C2 comprises the sequence as represented in SEQ ID NO:6. This sequence represents the 1200 pb preceding the site initiating the translation of the gene bglI in the construction C2.

In a third embodiment, the genome of *Trichoderma reesei* is modified so that the element regulating the promoting sequence for the gene xyn2 comprising the sequence represented in SEQ ID NO:2 is inserted between positions −396 and −341 with respect to the site initiating the translation of the gene coding for β-glucosidase. Preferentially, the element regulating the promoting sequence for the gene xyn1 consists of the sequence represented in SEQ ID NO:2. The sequence represented in SEQ ID NO:2 is therefore inserted between positions 854 and 909 of the sequence represented in SEQ ID NO:15.

This modified strain of *T. reesei* is called "construction C4" or "strain C4". In this embodiment, the strain has undergone a replacement of 55 pb of the promoter bglI by 55 pb of the element regulating the promoting sequence for the gene xyn2. Consequently the promoter of the gene bglI of the construction C4 comprises the sequence as represented in SEQ ID NO:8. This sequence represents the 1250 pb preceding the site initiating the translation of the gene bglI in the construction C4.

In a fourth embodiment, the genome of *Trichoderma reesei* is modified so that the element regulating the promoting sequence for the gene xyn2 comprising the sequence represented in SEQ ID NO:4 is inserted between positions −395 and 0 with respect to the site initiating the translation of the gene coding for β-glucosidase. The reference to the site initiating the translation of the gene coding for β-glucosidase means the position before the insertion of the mutation. Preferentially, the element regulating the promoting sequence for the gene xyn2 consists of the sequence represented in SEQ ID NO:4. The sequence represented in SEQ ID NO:4 is therefore inserted between positions 855 and 1250 of the sequence represented in SEQ ID NO:15.

This modified strain of *T. reesei* is called "construction C5" or "strain C5". In this embodiment, the strain has undergone a replacement of 395 pb of the promoter bglI by 235 pb of the element regulating the promoting sequence for the gene xyn2. In this embodiment, the sequence is juxtaposed with the site initiating the translation. Consequently the promoter of the gene bglI of the construction C5 comprises the sequence as represented in SEQ ID NO:9. This sequence represents the 1151 pb preceding the site initiating the translation of the gene bglI in the construction C5.

The strains C1, C2, C4 and C5 are inducible by sugars that exerted no or little inducing effect in the wild strains of *T. reesei*. In particular, these strains are inducible by xylose for the production of β-glucosidase.

Thus another subject of the invention relates to a strain of *Trichoderma reesei* the genome of which is modified so that the promoter of β-glucosidase comprises a sequence chosen from the sequence represented in SEQ ID NO:5, 6, 8 or 9. In one embodiment, the genome of the strain of the invention is modified so that the promoter of β-glucosidase comprises more preferentially the sequences represented in SEQ ID NO:8 or 9. In another embodiment, said genome comprises the sequence represented in SEQ ID NO:5.

The inventors have also developed a "construction C3" or "strain C3". In this construction, the genome of *Trichoderma reesei* is modified so that the element regulating the promoting sequence for the gene xyn1 comprising the sequence represented in SEQ ID NO:16 is inserted between positions −1121 and −893 with respect to the site initiating the translation of the gene coding for β-glucosidase. The sequence represented in SEQ ID NO:16 is therefore inserted between positions 129 and 357 of the sequence represented in SEQ ID NO:15.

In this embodiment, the strain has undergone a replacement of 228 pb of the promoter bglI by 230 pb of the element regulating the promoting sequence for the gene xyn1. Thus the promoter of the gene bglI of the construction C3 comprises the sequence as represented in SEQ ID NO:17. This sequence represents the 1250 pb preceding the site initiating the translation of the gene bglI in the construction C3.

The construction C3 is therefore characterised by an insertion of the element regulating the promoting sequence for the chosen gene xyn1 upstream of positions −800 and 0 with respect to the site initiating the translation of the gene coding for said cellulase. The strain C3 exhibits inducibility of the production of cellulases less than that observed for the other constructions. In particular, this construction is not inducible by xylose for the production of β-glucosidase.

Mutation Cassettes

In a second aspect, the invention relates to the mutation cassettes comprising a sequence chosen from the sequence represented in SEQ ID NO:10 to 14.

These cassettes are linear cassettes for obtaining a strain according to the invention from a wild strain of *T. reesei*.

"Cassette" or "mutation cassette" means a DNA structure allowing integration of a gene of interest or a fragment of said gene of interest in a target DNA fragment, typically according to the principle of homologous recombination. Preferentially, said cassette is linear and comprises a module comprising a marker gene and/or the gene to be integrated, this module being flanked on either side by DNA fragments homologous to those at the ends of the targeted integration site.

The cassette comprising the sequence as represented in SEQ ID NO:10 is used to obtain the strain C1, that is to say a strain of *T. reesei* the genome of which is modified so that the element regulating the promoting sequence for the xyn1 gene comprising the sequence represented in SEQ ID NO:1 is inserted between positions −628 and −411 with respect to the site initiating the translation of the bglI gene.

The cassette comprising the sequence as represented in SEQ ID NO:11 is used to obtain the strain C2, that is to say a strain of *T. reesei* the genome of which is modified so that the sequence promoting the gene xyn1 comprising the sequence represented in SEQ ID NO:3 is inserted between positions −633 and 0 with respect to the site initiating the translation of the gene bglI.

The cassette comprising the sequence as represented in SEQ ID NO:12 is used to obtain the strain C3, that is to say a strain of *T. reesei* the genome of which is modified so that the element regulating the promoting sequence for the gene xyn1 comprising the sequence represented in SEQ ID NO:16 is inserted between positions −1121 and −893 with respect to the site initiating the translation of the gene bglI.

The cassette comprising the sequence as represented in SEQ ID NO:13 is used to obtain the strain C4, that is to say a strain of *T. reesei* the genome of which is modified so that the element regulating the promoting sequence for the gene xyn2 comprising the sequence represented in SEQ ID NO:2 is inserted between positions −396 and −341 with respect to the site initiating the translation of the gene bglI.

The cassette comprising the sequence as represented in SEQ ID NO:14 is used to obtain the strain C5, that is to say a strain of *T. reesei* the genome of which is modified so that the sequence promoting the gene xyn2 comprising the sequence represented in SEQ ID NO:4 is inserted between positions −395 and 0 with respect to the site initiating the translation of the gene bglI.

Preferentially, the mutation cassettes are sequences represented in SEQ ID NO:10, 11, 13 and 14. In one embodiment, the mutation cassettes are the sequences represented in SEQ ID NO:13 or 14. In another embodiment said genome comprises the sequence represented in SEQ ID NO:10.

These cassettes are used to insert mutations in the genome of *T. reesei*. The mutation techniques are known to persons skilled in the art. It is possible to provide for various techniques ensuring the mutation of interest. It would be possible for example to use the mutation system known to persons skilled in the art, as well as insertions or other DNA modifications obtained by homologous recombination techniques.

Preferentially, this insertion is implemented by homologous recombination, typically by means of a vector or a linear cassette. The cassette is co-transformed with a vector that contains the selection marker.

According to the invention, "vector" means any DNA sequence in which it is possible to insert fragments of foreign nucleic acid, the vectors making it possible to introduce foreign DNA into the host cell. Examples of vectors are plasmids, cosmids, yeast artificial chromosomes (YACs), bacteria artificial chromosomes (BACs) and artificial chromosomes derived from the P1 bacteriophage (PACs), and vectors derived from viruses. The vector according to the invention allows the introduction of a mutation and/or of a deletion.

Typically, the nucleic acid as described previously can be bound operationally to a promoter, a terminator or any other sequence necessary for expansion thereof in the host cell.

In a preferred embodiment, the vector according to the invention carries a selection marker. Alternatively, the selection marker is present on a second vector.

"Selection marker" means a gene the expression of which confers on the cells that contain it a characteristic making it possible to select them. It is a case for example of a gene resistant to antibiotics or a gene conferring independence vis-à-vis a particular metabolite.

The mutation cassette may then be amplified according to conventional techniques well known to persons skilled in the art, typically by a method chosen from conventional cloning, PCR fusion, or in vivo cloning in yeast by PCR. In the context of the invention, this cassette is preferentially amplified by PCR.

The mutation cassette is next introduced by recombination into a strain of *T. reesei* that does not express a gene of the selection marker.

After culture, the mutant cells that have incorporated the mutation cassette are selected according to the expression or not of the selection marker; the clones that have been transformed expressing said selection marker.

In a preferred embodiment, said mutation cassette is a linear cassette. This mutation cassette can be obtained after cloning in a vector as described above and transformation of *T. reesei*. Typically, the integration of a gene of interest in a target DNA fragment is done in accordance with the principle of homologous recombination. For this purpose, a linear cassette comprises a module comprising the DNA part to be integrated flanked on either side by DNA fragments homologous to those of the ends of the targeted integration site. After transformation of the fungus with the cassette by suitable methods, homologous recombination between the sequences of the construction and the corresponding regions of the target gene results in the replacement of the target DNA fragment by the integration cassette.

At the same time, a second cassette comprises the gene of the selective marker.

Thus, in this embodiment, said mutation cassette may be a substitution cassette allowing:

firstly, the excision of a fragment of the bgII promoter, and
secondly, the insertion of an element regulating the promoting sequence for an xyn1 or xyn2 gene.

Uses of the Strains of the Invention

In a third aspect, the invention relates to the use of the strain according to the invention for the production of cellulolytic enzymes, preferably in the presence of an inducing substrate chosen from xylane; xylose; oligomers of xylose; arabinose; a hemicellulose hydrolysate; and mixtures thereof. These inducers may be mixed with an inducing substrate for cellulases, such as lactose or cellulose, in order to obtain a stronger induction.

Another subject matter of the invention also relates to the use of the strain according to the invention for hydrolysis of cellulose into glucose.

Another subject matter of the invention relates to the use of the strain according to the invention for producing products biosourced from glucose.

"Biosourced product" means any product that is not of fossil origin and does not contain an organic product of fossil origin. The term "product of fossil origin" means any organic product issuing from crude oil or coal or derivatives of crude oil or coal. Preferentially, in the context of the invention, it is an alcohol, such as isopropanol, butanol or ethanol.

Finally, another subject matter of the invention relates to the use of the strain according to the invention for producing biofuels.

According to the invention, the term "biofuel" can be defined as any product issuing from the transformation of biomass and able to be used for energy purposes. Firstly, and without wishing to be limited, mention can be made by way of example of biogas, products able to be incorporated (optionally after subsequent transformation) in a fuel or be a complete fuel, such as alcohols (ethanol, butanol, and/or isopropanol according to the type of fermentative organism used), solvents (acetone), acids (butyric), lipids and derivatives thereof (short or long chain fatty acids, fatty acid esters), and hydrogen. Preferably, the biofuel according to the invention is an alcohol, for example ethanol, butanol and/or isopropanol. More preferentially, the biofuel according to the invention is ethanol.

In a particular embodiment, the invention relates to a method for producing (3-glucosidase comprising the step of culture of a strain of *Trichoderma reesei* the genome of which is modified by the insertion of at least one element regulating the promoting sequence for a gene chosen from xyn1 and xyn2, in the promoting sequence for the gene coding for β-glucosidase, it being understood that:

the element regulating the promoting sequence for the gene xyn1 comprises the sequence represented in SEQ ID NO:1 or the sequence represented in SEQ ID NO:3;
the element regulating the promoting sequence for the gene xyn2 comprises the sequence represented in SEQ ID NO:2 or the sequence represented in SEQ ID NO:4, in a culture medium comprising a substrate chosen from lactose and cellulose or one of the mixtures thereof; and
an inducing substrate chosen from xylane; xylose; xylose oligomer; arabinose; a composition comprising glucose, xylose, galactose, mannose, cellobiose and acetic acid; and mixtures thereof.

All the previously stated technical features apply here.

Finally, the invention relates to a method for producing a biofuel, preferably ethanol, from cellulosic or lignocellulosic materials, comprising steps of pretreatment of a cellulosic or lignocellulosic substrate, enzymatic hydrolysis of the pretreated substrate and then alcoholic fermentation of the hydrolysate obtained, in which use is made, for producing the cellulolytic and/or hemicellulolytic enzymes, of a strain of *Trichoderma reesei* according to the invention in the presence of an inducing substrate chosen from xylane; xylose, xylose oligomers; arabinose; a hemicellulose hydrolysate; and mixtures thereof.

All the previously stated technical features apply here.

DESCRIPTION OF THE SEQUENCES

SEQ ID NO:1 and SEQ ID NO:3 represent an element regulating the promoting sequence for the gene xyn1.

SEQ ID NO:2 and SEQ ID NO:4 represent an element regulating the promoting sequence for the gene xyn2.

SEQ ID NO:5 represents the 1250 pb preceding the site initiating the translation of the gene bglI in the construction C1.

SEQ ID NO:6 represents the 1200 pb preceding the site initiating the translation of the gene bglI in the construction C2.

SEQ ID NO:7 represents the 1250 pb preceding the site initiating the translation of the gene bglI in the construction C3.

SEQ ID NO:8 represents the 1250 pb preceding the site initiating the translation of the gene bglI in the construction C4.

SEQ ID NO:9 represents the 1151 pb preceding the site initiating the translation of the gene bglI in the construction C5.

SEQ ID NO:10 represents the cassette used to obtain the construction C1.

SEQ ID NO:11 represents the cassette used to obtain the construction C2.

SEQ ID NO:12 represents the cassette used to obtain the construction C3.

SEQ ID NO:13 represents the cassette used to obtain the construction C4.

SEQ ID NO:14 represents the cassette used to obtain the construction C5.

SEQ ID NO:15 represents the 1250 pb preceding the site initiating the translation of the gene bglI in the wild strain of *Trichoderma reesei*. It is therefore a case of a fragment of the native promoter of bglI in *T. reesei*.

SEQ ID NO:16 represents an element regulating the promoting sequence for the gene xyn1. This sequence also comprises the sequence as represented in SEQ ID NO:1.

For reasons of clarity, the following table summarises the correspondences between:
- the references to the positions with respect to the site initiating the translation of the gene of β-glucosidase; and
- the references to the positions with respect to the sequence represented in SEQ ID NO:15.

| Positions with respect to the site initiating the translation of the gene of β-glucosidase | Positions with respect to the sequence represented in SEQ ID NO: 15 |
| --- | --- |
| between −628 and −411 | between 622 and 839 |
| between −633 and 0 | between 617 and 1250 |
| between −396 and −341 | between 854 and 909 |
| between −395 and 0 | between 855 and 1250 |
| between −1121 and −893 | between 129 and 357 |
| −1224 | 26 |
| −1218 | 32 |
| −881 | 369 |
| −874 | 376 |
| −811 | 439 |
| −805 | 445 |

LEGENDS OF THE FIGURES

FIG. 1: diagram of the 4 constructions of the promoter of bglI

C1 to C3 contain sequences of the xyn1 promoter, and C4 and C5 contain units issuing from the xyn2 promoter. In these constructions, the HAP2/3/5 and Xyr1 units identified in the promoter of bglI are maintained.

FIG. 2: Ratio of bglI transcripts at 4, 24 and 48 hours in the modified strains and the reference strain with respect to the level of bglI transcripts at T0 (standardised to 1). The expression was standardised with respect to the sar1 gene the expression of which is constant. It is a case of the mean values obtained in two clones per construction, and of two cultures/clone, except for C2.

Figure 2A:
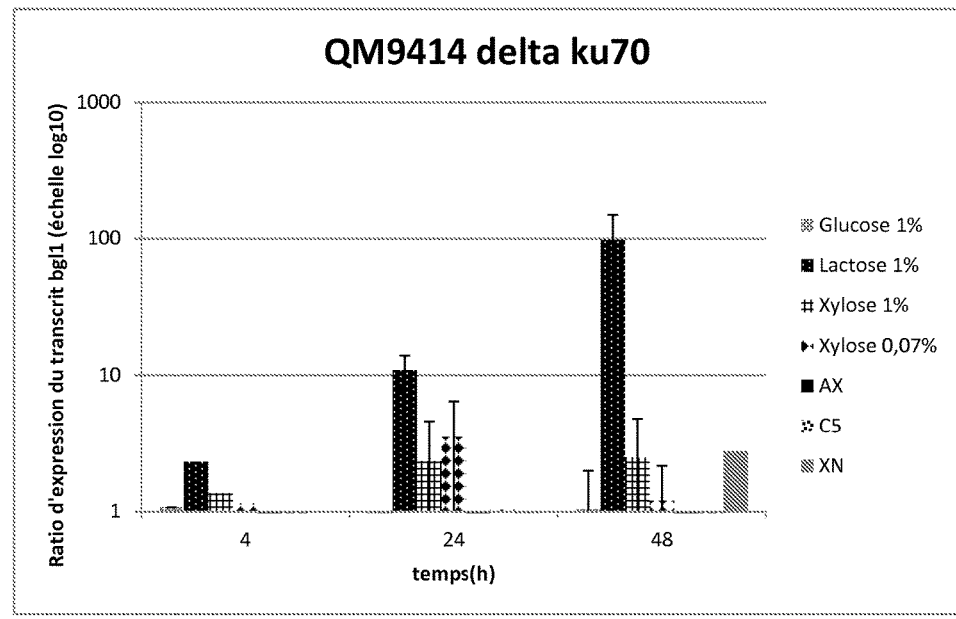
Figure 2B:
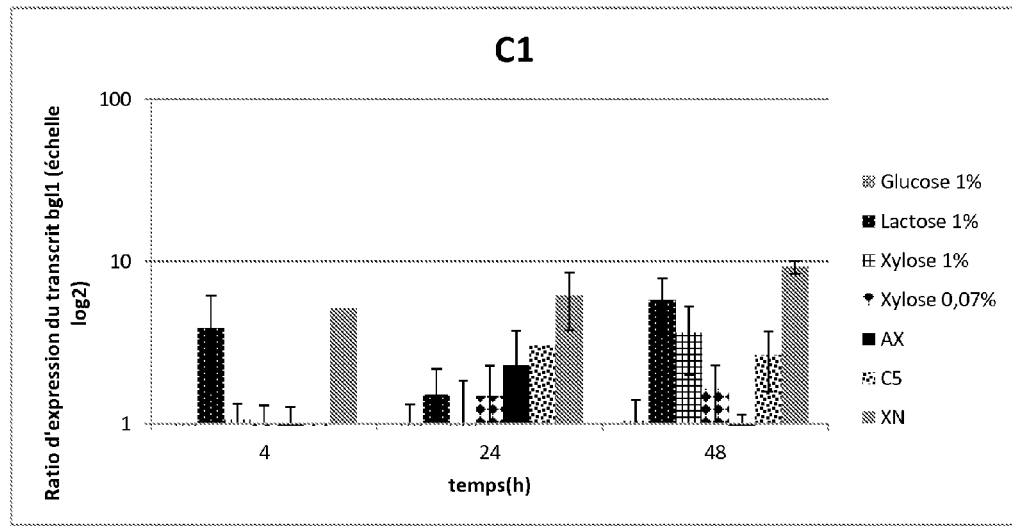
Figure 2C:
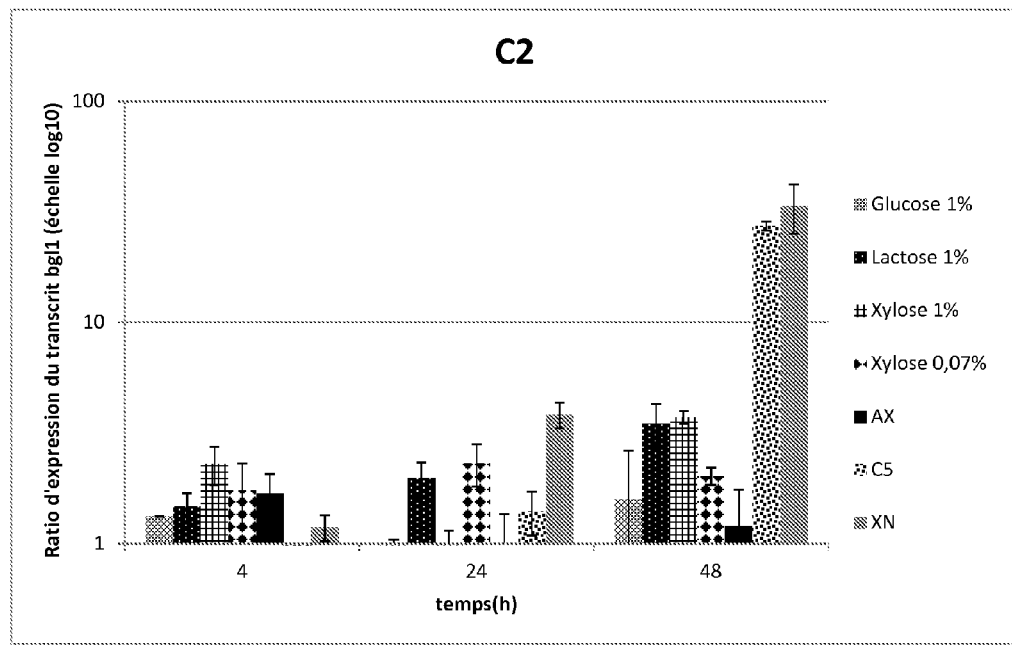
Figure 2D:
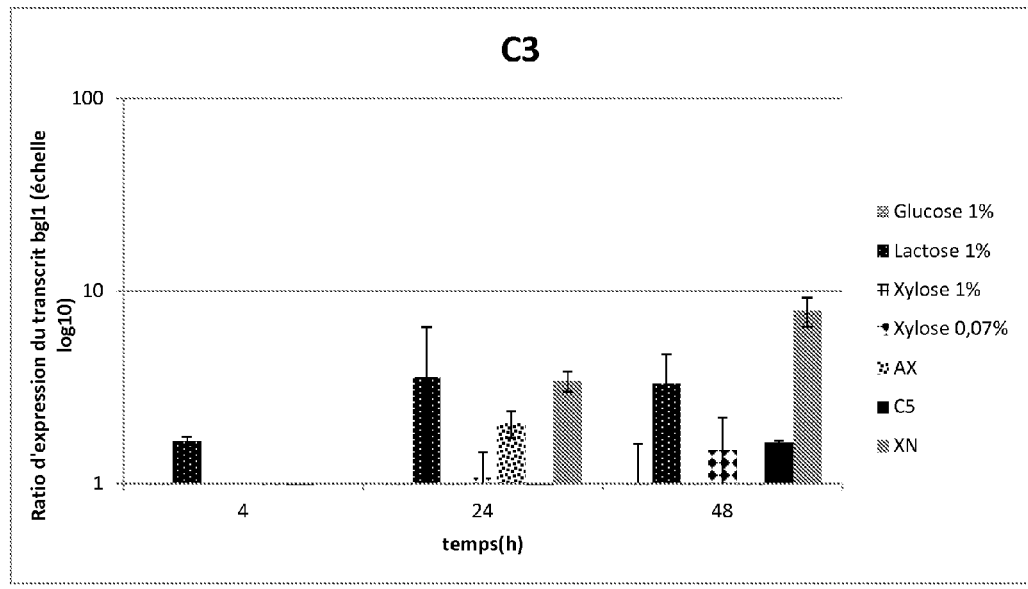
Figure 2E:
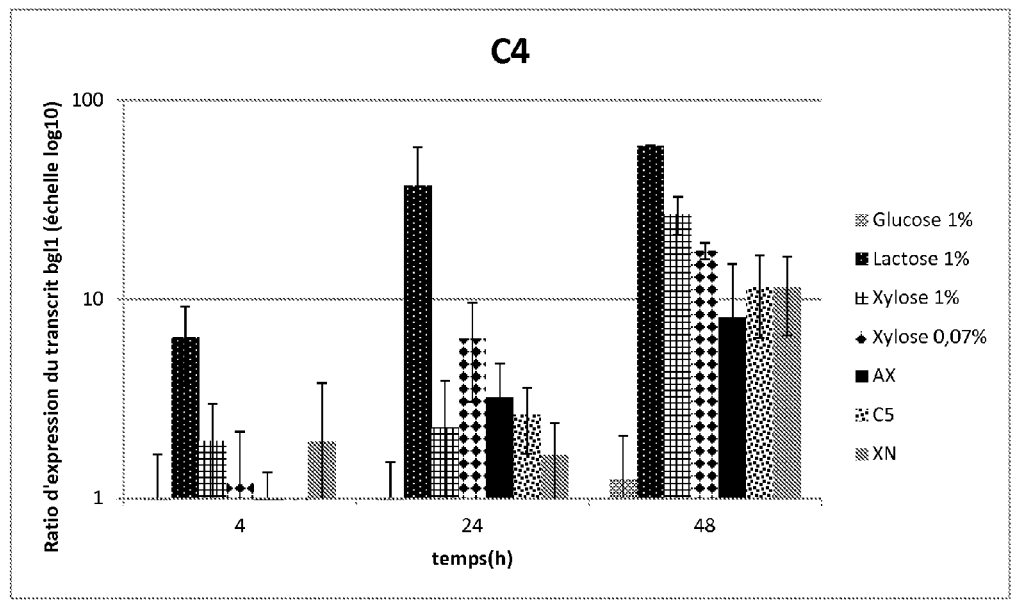
Figure 2F:
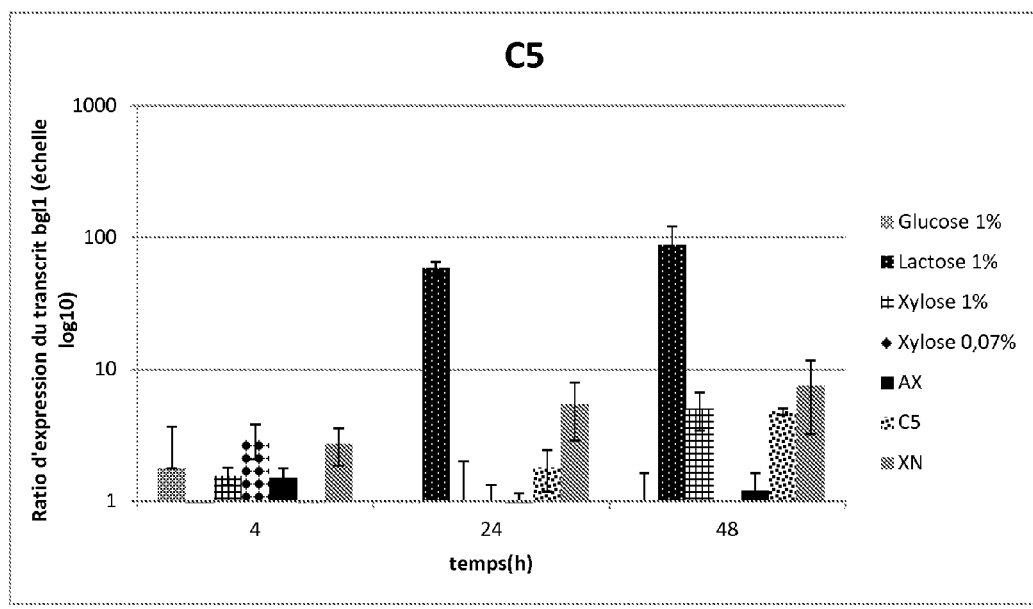

FIG. 2A shows the results for QM9414 Δku70 pyr4−;
FIG. 2B shows the results for construction C1;
FIG. 2C shows the results for construction C2;
FIG. 2D shows the results for construction C3;
FIG. 2E shows the results for construction C4;
FIG. 2F shows the results for construction C5.

The substrates tested are as follows:
"1% glucose";
"1% lactose";
"1% xylose";
"0.07% xylose", which corresponds to a mixture of 0.075% xylose and 1% glycerol;
"Ax" which corresponds to a mixture of 1 mM L-arabinose and 1 mM D-xylose;
"XN", which corresponds to 1% xylane; and
"C5", which corresponds to a hemicellulose hydrolysate.

The following examples illustrate the invention but in no way limit the scope thereof.

Figure 3:
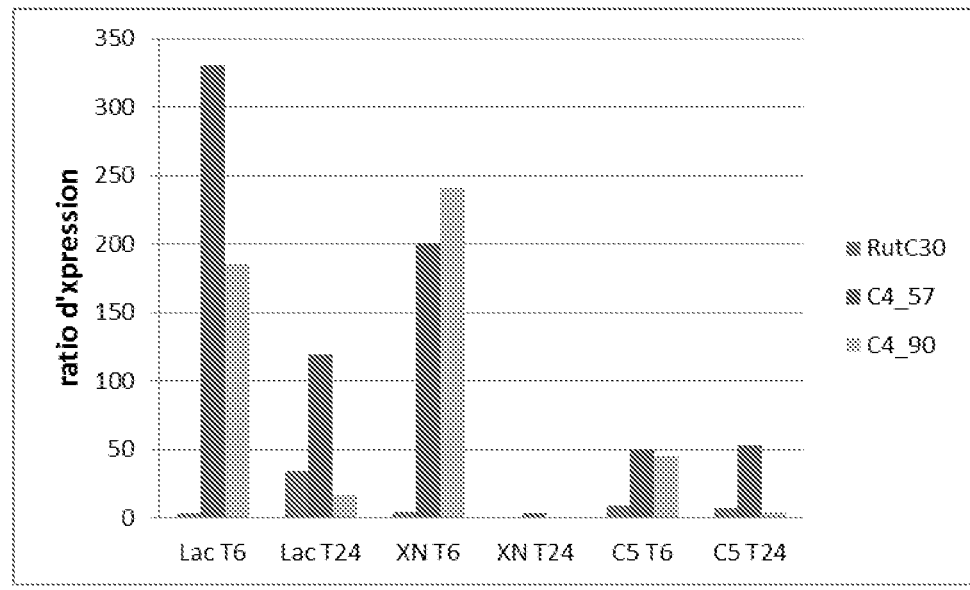

FIG. 3: ratios of bglI transcripts at 6 and 24 hours after additions of respective lactose (Lac), or xylane (XN) substrate or hemicellulose hydrolysate in two strains comprising the C4 construction with respect to the level of bglI transcripts in the reference strain RutC30 on glucose. The expression was standardised with respect to the sar1 gene the expression of which is constant.

Figure 4:
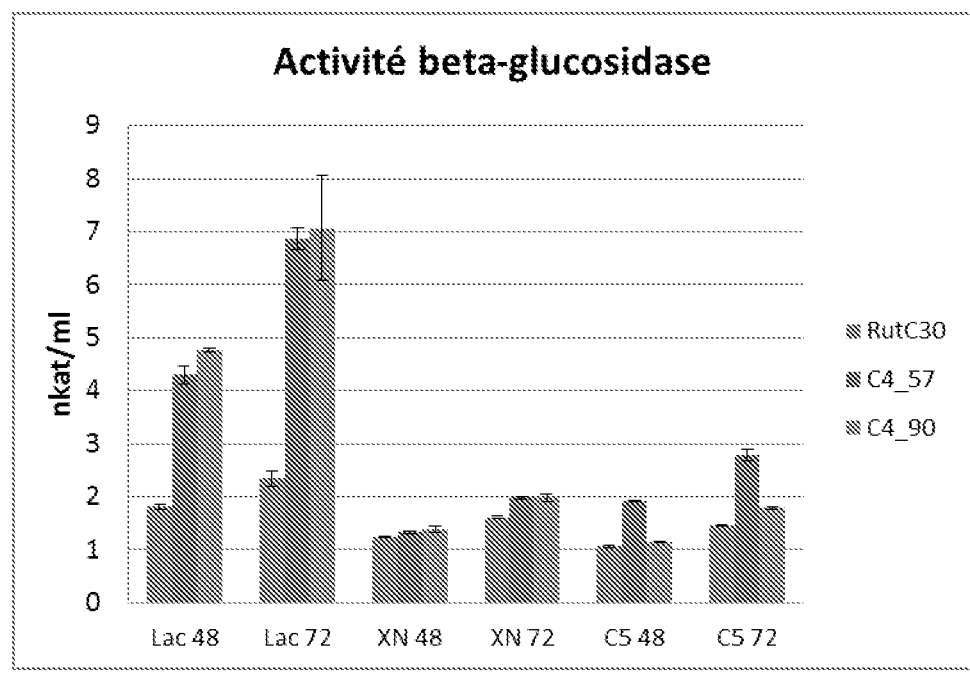

FIG. 4: beta-glucosidase activities measured in the supernatants of the cultures of the reference strain RutC30 and the two clones comprising the C4 construction, 48 or 72 hours after addition of the lactose (Lac) or xylane (XN) substrates or hemicellulose hydrolysate.

EXAMPLES

Example 1

The inventors developed several exemplifying constructions C1, C2, C4 and C5 and a construction C3 used to show the positive effect of the xyn1 unit, as follows:

Construction C1: replacement of a fragment of the promoter of bglI by a minimum sequence allowing regulation of the promoter of the xyn1 gene.

Construction C2: replacement of a fragment of the promoter of bglI by the minimum promoter of the xyn1 gene.

Construction C3: replacement of a fragment situated upstream of the cis elements of the promoter of bglI by a minimum sequence allowing regulation of the promoter of the xyn1 gene.

Construction C4: replacement of a fragment of the promoter of bglI by a minimum sequence allowing regulation of the promoter of the xyn2 gene.

Construction C5: replacement of a fragment of the promoter of bglI by the minimum promoter of the xyn2 gene.

These constructions are shown schematically in FIG. 1.

Materials and Methods

Production of the Constructions

The constructions were produced by means of the Gibson Assembly Cloning Kit (New England Biolabs).

The primers for amplifying the DNA fragments to be associated are designed via the software http://nebuilder.neb.com/. These primers were designed so as to have a tail of 15 to 80 pb, which is complementary to the end of the fragment to be attached.

The vector plasmid used is the bacterial plasmid pUC19, carrying the gene for resistance to ampicillin ampR. Before being used as a vector, this plasmid was opened by the restriction enzymes XhoI and EcoRI (New England Biolabs) and purified on column (PCR Purification kit, Qiagen).

Once the fragments were associated, the plasmid was amplified by transformation in E. coli (supplied in the kit) and extracted (Plasmid Plus Midi kit, Qiagen).

The substitution cassettes were amplified using the plasmid extracted by PCR.

Transformation of T. reesei

T. reesei was cultivated in Roux phials containing 200 ml of Potato Dextrose Broth (Difco Laboratories USA) for 3 days at 30° C. without agitating. The mycelium was collected by filtration on sterile gauze and washed in 200 ml of KPAm buffer (0.6 M $(NH_4)_2SO_4$; 25 mM $KH_2PO_4$; pH 5.8) via incubation of 30 minutes at 37° C., 150 rpm. After a new step of filtration on sterile gauze, the fungicidal wall of the cells was digested by incubation with 100 ml of KPAm buffer containing 30 mg/ml of Glucanex (Novozymes). The cells were next passed over sintered glass, recovered in the filtrate and transferred into five 20 ml Corex tubes. They were next precipitated by centrifugation (4000 rpm, 5 minutes, 4° C.). Each pellet was washed with 20 ml of CTS10 buffer (0.4 M saccharose, 100 mM Tris-HCl pH 7.5, $CaCl_2$ 10 mM) and after centrifugation (4000 rpm, 5 minutes, 4° C.) the protoplasts were collected in 3 tubes. They were resuspended in 20 ml of CTS10 and precipitated by a further centrifugation (4000 rpm, 5 minutes, 4° C.). Finally they were collected in a single tube and washed for a last time with 10 ml of CTS10. After centrifugation (4000 rpm, 5 minutes, 4° C.), the protoplasts were recovered in 5 ml of CTS50 buffer (0.4 M saccharose, 100 mM Tris-HCl pH 7.5; 50 mM $CaCl_2$) in order to be counted under optical microscope on a Malassez cell. Finally, the protoplast solution was centrifuged (4000 rpm, 5 minutes, 4° C.) and the cells resuspended in CTS50 in a volume V calculated for the obtaining of a final concentration of $2 \cdot 10^8$ cells/ml.

45 µl of protoplast solution at $2 \cdot 10^8$ cells/ml was put in contact with 5 µg of the cassette and 1 µg of the fragment carrying the transformation marker in a 50 ml Falcon tube. The total volume of the DNA solutions used did not exceed 5 µl. After 10 minutes of incubation of the mixture at ambient temperature, 500 µl of PEG buffer (60% 4000 polyethylene glycol; 10 mM Tris HCl; 50 mM $CaCl_2$; pH 7.5) was added. After 20 minutes of incubation at ambient temperature the cell suspension was extended with 450 µl of CTS50 in order to reach a final volume of 1 ml. Finally, the cells were diluted in 40 ml of selection overlay medium (gelosed selective medium with 0.8 M saccharose added for maintaining the osmotic pressure of the protoplasts) hot (between 50° C. and 55° C.) before being spread over 5 dishes (8 ml/dish) of selection medium (gelose selective medium with 0.2 M saccharose added). The dishes were then incubated at 30° C. for 3-4 days in order to observe the germination of the spores. The transformants obtained were next purified in four successive transplant steps.

T. reesei Cultures 50 ml of rich culture medium (PD, Difco) was seeded with spores of each strain and incubated at 30° C. under agitation for three days. Next the mycelium was filtered on sterile gauze, wash twice with physiological water and put back in suspension in minimum medium (50 mM $K_2HPO_4$; 30 mM $(NH_4)_2SO_4$; 1.2 mM $MgSO_4$; 100 mM maleic acid; trace elements ($FeSO_4$ 5 mg/l; $MnSO_4$ 1.4 mg/l; $ZnSO_4$ 1.4 mg/l; $CoCl_2$ 3.7 mg/l); pH 6) with a carbon source added (1% glucose, 1% lactose, 1% or 0.075% xylose) and uridine (10 mM) for the QM 9414 Δku70 pyr4 strain. The cultures were once again incubated at 30° C. for 48 hours. At TO, T4, T24 and T48 hours, 2×2 ml of culture was taken off and centrifuged and the supernatant transferred into a new tube. The pellet was dried on Whatman paper and frozen in liquid nitrogen before storage at −80° C. until the RNA was extracted. The supernatants were placed at −20° C.

Extraction of RNA, Retrotranscription and Quantitative PCR

The frozen mycelium was taken up in 700 µl of RLT buffer (RNeasy Mini Kit, Qiagen) with 7 µl of pure ground β-mercapto-ethanol added in tubes containing beads (Lysing matrix C, MP Biomedicals) with the Fastprep (MP Biomedicals) homogeniser for 40 seconds at maximum speed. The tubes were next centrifuged for 5 minutes (4° C., 14,000 rpm) and the supernatant transferred into QIAshredder (Qiagen) columns in order to separate the liquid phase from the cell debris. After centrifugation for 2 minutes (4° C., 10,000 rpm), 0.5 vol of ethanol was added to the eluate, which was then deposited on a column of the RNeasy extraction kit (Qiagen). After centrifugation, digestion by DNase (RNase-Free DNase Set, Qiagen) on column and washings were carried out in accordance with the instructions of the supplier. The RNA was diluted with 100 µl of DEPC water. The concentrations of RNA extracted were determined by assay with Qubit 2.0 (Invitrogen) and 500 ng was used for the reverse transcription reaction (iScript Kit, Biorad). 5 µl of the reaction diluted to ⅕ was used as a matrix for the qPCR. A negative check with the same quantity of RNA not retrotranscribed was carried out for each sample in order to confirm the absence of DNA. Each point was carried in duplicate. The quantities of bglI transcripts were standardised with respect to the sar1 gene and with respect to the quantity of bglI transcripts at TO.

Results

The constructions C1, C2 and C3 contain the unit of 217 pb identified as being responsible for induction of the xyn1 gene, this sequence being represented in SEQ ID NO:1.

As for the constructions C4 and C5, these contain the 55 pb's essential for induction of the xyn2 gene (Zeilinger et al., 1996), this sequence being represented in SEQ ID NO:2.

For C1, C2, C4 and C5, the units were placed at the same distance from the start of the transcription (symbolised by an arrow in FIG. 1) as in their original genes.

Thus the distance of 153 pb between the start of the xyn1 and the start of xyn1 transcription is kept in C1 and C2, and the distance of 82 pb observed in xyn2 is kept in constructions C4 and C5.

In the construction C3, the unit xyn1 was placed upstream of the cis elements of the bglI promoter in order to demonstrate the effect of position of the xyn1 unit.

In the constructions C2 and C5, in addition to the unit comprising the induction elements, the entire sequence downstream of the genes xyn1 and xyn2 as far as the start of the coding sequence (and therefore comprising the 5'UTR sequence) was inserted. Since the 5'UTR is shorter in the xyn1 and xyn2 genes compared with the bglI gene, the total length upstream of the site initiating the translation (that is to say the ATG) is consequently shorter than in bglI.

After transformation, checks by PCR and by sequencing of the locus were carried out in order to confirm the correct insertion of the units. Two clones for each construction were chosen for analysis (with the exception of the construction C2, for which only one clone could be obtained). For these, the modified strains and the starting strain QM9414 Δku70 pyr4− were put in the presence of various carbon sources:
- glucose (non-inducing control),
- lactose (inducing control),
- 1% and 0.075% xylose (test conditions),
- a mixture of arabinose and xylose (each 1 mM),
- xylane (1%) or
- a hemicellulose hydrolysate containing 3.5 g/l of xylose, 0.6 g/l of mannose, 0.16 g/l of galactose and 0.4 g/l of glucose.

The expression of the bglI gene was next determined by RT-qPCR.

The results are presented in FIG. 2.

It is found that the bglI gene is significantly induced only in the presence of lactose in the reference strain (panel A). This induction is reduced, but still present, in strains that have integrated the constructions C1, C2 and C3, that is to say containing the unit xyn1 in the bglI promoter. The strains having the constructions C4 and C5, on the other hand, keep a significant induction (from 60 to 90 times) by lactose.

Unlike the reference strain, an induction of the bglI gene in the C1, C2, C4 and C5 genes by 1% xylose, and even more weakly with 0.075% xylose, is also observed. This induction becomes 5 to 10 times stronger in the case of the C4 construction, compared with the C1, C2 and C5 strains.

The presence of xylane and hemicellulose hydrolysate also leads to an induction in these four strains, approximately of the same order of magnitude as in the presence of 1% xylose.

On the other hand, the C3 construction confers inducibility only in the presence of xylane, but not in the presence of pentose monomers, emphasising the importance of the correct positioning of the xyn1 unit in the promoter and with respect to the initiation of the transcription and translation: if the xyn1 unit is placed between −1121 and −893 pb before the site initiating the translation of the bglI gene, no induction by the pentose monomers is observed.

The sequence between the xyn1 and xyn2 units respectively, and the initiating codon also has an effect on inducibility: in the strains having the C2 construction, the bglI gene is induced more in the presence of xylane and hemicellulose hydrolysate than in strains having the C1 construction. The region downstream of the xyn1 unit, also comprising the 5'-UTR of the xyn1 gene, therefore has a positive effect on inducibility by xylane and derivatives thereof.

In the case of the 5'-UTR sequence of the xyn2 gene, exactly the opposite is observed. This is because the presence of this sequence shows rather a weaker induction of bglI in the presence of xylose or xylane. The integration of the 55 pb issuing from the xyn2 promoter is therefore the best choice for transferring this inducibility.

All the results show that it is possible to change the inducibility of the bglI promoter by inserting the induction units issuing from the xylanase genes.

According to the type of unit and the location, this induction is strong to a greater or lesser extent.

Thus the inventors showed that it was possible to change the expression profile of β-glucosidase, but also of cellulases in the presence of inexpensive inducers such as xylose and thus to obtain a cocktail having balanced cellulase/β-glucosidase and xylanase activities under these conditions.

Example 2

The inventors also modified the promoter of the bglI gene in a *T. reesei* RutC30 hyperproducing strain.

Materials and Methods

Measurement of the β-Glucosidase Activity

The β-glucosidase activities are determined by hydrolysis of the p-nitrophenol-glucopyranoside (pNPG) substrate in glucose and p-nitrophenol, which absorbs light at 410 nm. The reaction mixture contains 90 µl of pNPG substrate (5 mM in 50 mM citrate buffer at pH 4.8) and 10 µl of supernatant of the cultures, optionally previously diluted.

The mixture is incubated for 30 minutes at 50° C., and then the reaction is stopped by adding 100 µl of 2% $Na_2CO_3$ after having placed it on ice. The samples are next incubated at ambient temperature for 20 minutes, before reading at 410 nm. Quantification is done by means of a p-nitrophenol range from 12.5 to 200 µM, and after subtraction of the values of an enzyme blank containing 10 µl of culture supernatant with 90 µl of citrate buffer and a substrate blank where the culture supernatant is replaced by 10 µl of substrate buffer. The values are averages of double measurements.

Results

The modified promoter that gave the best results in the model QM9414 strain, corresponding to the C4 construction, was introduced into the *T. reesei* RutC30 hyperproducing strain.

To modify the bglI promoter, the RutC30 strain underwent co-transformation with 5 µg of the cassette carrying the C4 construction and 1 µg of the fragment carrying the selection marker. Transformation and screening were carried out as described previously. After screening around a hundred clones, several positive clones that had integrated the cassette at the correct place in the genome were identified. Two clones for which the integration of the sequence was confirmed by sequencing were put in culture in a rich medium, before being transferred into a minimum medium containing either 1% glucose or 1% lactose or 1% xylane or hemicellulose hydrolysate. Samplings were made at T=6 hours and 24 hours.

RNA was extracted and the expression of the bglI gene determined by RT-qPCR. In parallel, the activity of beta-glucosidase was measured in the supernatants sampled at T=48 hours and 72 hours. The results are presented in FIGS. 3 and 4.

It should be noted that the level of expression of the bglI gene in the modified strains is multiplied by a factor of 60 to 100 in the presence of lactose after 6 hours of exposure, compared with the RutC30 strain.

This increase in the level of transcript results in an increase in the activity by a factor of 2 and 3 after 48 and 72 hours respectively, in the strains with modified promoter. It is also found that the level of expression of the bglI gene in these strains in the presence of xylane increases by a factor of 50 to 60 after 6 hours and on a hemicellulose hydrolysate by a factor of 5 to 6, compared with the RutC30 reference strain.

The beta-glucosidase activity increases only slightly in the presence of xylane, but double on a hemicellulose hydrolysate for one of the two clones. The results with the RutC30 hyperproducing strain therefore confirmed that the integration of the xyn2 unit in the bglI promoter leads to an increase in the expression of the gene. In this strain, which is not subject to catabolic repression, catabolite repression, unlike the QM414 strain, the increase is observed not only on pentoses, but also on lactose.

The invention claimed is:

1. A strain of *Trichoderma reesei* having a genome modified by the insertion of at least one element regulating the promoting sequence for a gene chosen from xyn1 and xyn2, in the promoting sequence for a gene coding for a cellulase,
wherein:
the element regulating the promoting sequence for the xyn1 gene comprises the sequence of SEQ ID NO:1 or the sequence of SEQ ID NO:3;
the element regulating the promoting sequence for the xyn2 gene comprises the sequence of SEQ ID NO:2 or the sequence of SEQ ID NO:4.

2. A strain according to claim 1, wherein said insertion takes place between positions −800 and 0 with respect to the site initiating the translation of the gene coding for said cellulase.

3. A strain according to claim 1, wherein said cellulase is chosen from exo-β-1,4-glucanases or cellobiohydrolases, endo-β-1,4-glucosidases and β-glucosidases.

4. A strain according to claim 1, wherein said cellulase is β-glucosidase.

5. A strain according to claim 4, wherein the promoter of β-glucosidase comprises a sequence chosen from the sequence of SEQ ID NO:5, 6, 8 or 9.

6. A strain according to claim 1, wherein the production of cellulase by said strain is inducible by an inducing substrate chosen from:
xylane;
xylose;
oligomers of xylose;
arabinose;
a composition comprising glucose, xylose, galactose, mannose, cellobiose, and acetic acid; and
mixtures thereof.

7. A strain according to claim 1, wherein the production of cellulase by said strain is inducible by a substrate chosen from lactose and cellulose or one of the mixtures thereof with an inducing substrate chosen from:
xylane;
xylose;
oligomers of xylose;
arabinose;
a composition comprising glucose, xylose, galactose, mannose, cellobiose, and acetic acid; and
mixtures thereof.

8. A strain according to claim 1, wherein the production of cellulase by said strain is inducible by:
lactose;
xylose; and
a mixture of lactose and xylose.

9. A strain according to claim 4, wherein the element regulating the sequence promoting the xyn1 gene comprises the sequence of SEQ ID NO:1 and is inserted between positions −628 and −411 with respect to the site initiating the translation of the gene coding for β-glucosidase.

10. A strain according to claim 4, wherein the element regulating the sequence promoting the xyn1 gene comprises the sequence of SEQ ID NO:3 and is inserted between positions −633 and 0 with respect to the site initiating the translation of the gene coding for β-glucosidase.

11. A strain according to claim 4, wherein the element regulating the sequence promoting the xyn2 gene comprises the sequence of SEQ ID NO:2 and is inserted between positions −396 and −341 with respect to the site initiating the translation of the gene coding for β-glucosidase.

12. A strain according to claim 4, wherein the element regulating the sequence promoting the xyn2 gene comprises the sequence of SEQ ID NO:4 and is inserted between positions −395 and 0 with respect to the site initiating the translation of the gene coding for β-glucosidase.

13. A mutation cassette comprising a sequence chosen from the sequences of SEQ ID NO:10, 11, 13 and 14.

14. A method for producing cellulolytic enzymes comprising the step of culturing a strain according to claim 1.

15. A method for producing β-glucosidase, comprising the step of culturing a strain of *Trichoderma reesei* having a genome modified by the insertion of at least one element regulating the promoting sequence for a gene chosen from xyn1 and xyn2, in the promoting sequence for the gene coding for β-glucosidase,
wherein:
the element regulating the promoting sequence for the xyn1 gene comprises the sequence of SEQ ID NO:1 or the sequence of SEQ ID NO:3;
the element regulating the promoting sequence for the xyn2 gene comprises the sequence of SEQ ID NO:2 or the sequence of SEQ ID NO:4, in a culture medium comprising
a substrate chosen from lactose and cellulose or one of the mixtures thereof; and
an inducing substrate chosen from xylane; xylose; oligomers of xylose; arabinose; a composition comprising glucose, xylose, galactose, mannose, cellobiose and acetic acid; and mixtures thereof.

* * * * *